US008765924B2

(12) United States Patent
Abuchowski et al.

(10) Patent No.: US 8,765,924 B2
(45) Date of Patent: Jul. 1, 2014

(54) MODIFIED ERYTHROPOIETIN

(75) Inventors: Abraham Abuchowski, Califon, NJ (US); Lihsyng Stanford Lee, Cranbury, NJ (US)

(73) Assignee: Prolong Pharmaceuticals, Inc., South Plainfield, NJ (US)

( * ) Notice: Subject to any disclaimer, the term of this patent is extended or adjusted under 35 U.S.C. 154(b) by 970 days.

(21) Appl. No.: 12/376,333

(22) PCT Filed: Jul. 16, 2007

(86) PCT No.: PCT/US2007/073629
§ 371 (c)(1),
(2), (4) Date: Mar. 4, 2010

(87) PCT Pub. No.: WO2008/019214
PCT Pub. Date: Feb. 14, 2008

(65) Prior Publication Data
US 2010/0184655 A1 Jul. 22, 2010

Related U.S. Application Data

(60) Provisional application No. 60/835,429, filed on Aug. 4, 2006.

(51) Int. Cl.
C07K 1/06 (2006.01)
C07K 1/10 (2006.01)
C07K 1/107 (2006.01)
C07K 14/505 (2006.01)
A61K 38/18 (2006.01)
A61K 38/00 (2006.01)

(52) U.S. Cl.
CPC ............ *C07K 14/505* (2013.01); *A61K 38/00* (2013.01)
USPC ............ 530/421; 530/397; 530/402; 514/7.7

(58) Field of Classification Search
None
See application file for complete search history.

(56) References Cited

U.S. PATENT DOCUMENTS

| 5,122,614 | A | 6/1992 | Zalipsky |
| 5,272,071 | A | 12/1993 | Chappel |
| 5,441,868 | A | 8/1995 | Lin |
| 5,547,933 | A | 8/1996 | Lin |
| 5,618,698 | A | 4/1997 | Lin |
| 5,621,080 | A | 4/1997 | Lin |
| 5,641,670 | A | 6/1997 | Treco et al. |
| 5,733,761 | A | 3/1998 | Treco et al. |
| 5,756,349 | A | 5/1998 | Lin |
| 5,955,422 | A | 9/1999 | Lin |
| 5,981,214 | A | 11/1999 | Skoultchi |
| 5,985,265 | A | 11/1999 | Kinstler et al. |
| 5,994,122 | A | 11/1999 | Cooper et al. |
| 6,077,939 | A | 6/2000 | Wei et al. |
| 6,340,742 | B1 | 1/2002 | Burg et al. |
| 6,583,272 | B1 | 6/2003 | Bailon |
| 7,074,397 | B1 | 7/2006 | Matthews |
| 7,128,913 | B2 | 10/2006 | Burg et al. |
| 7,169,754 | B2 | 1/2007 | Papadimitriou |
| 7,202,208 | B2 | 4/2007 | Papadimitriou |
| 7,208,145 | B2 | 4/2007 | McManus et al. |
| 2002/0115833 | A1 | 8/2002 | Burg et al. |
| 2003/0077753 | A1 | 4/2003 | Tischer |
| 2003/0120045 | A1 | 6/2003 | Bailon |
| 2003/0166566 | A1 | 9/2003 | Kinstler et al. |
| 2004/0082765 | A1 | 4/2004 | Nakamura et al. |
| 2004/0127419 | A1* | 7/2004 | Hu .................................. 514/12 |
| 2004/0266690 | A1 | 12/2004 | Pool |
| 2005/0114037 | A1 | 5/2005 | Desjarlais et al. |
| 2005/0147661 | A1 | 7/2005 | Tabata et al. |
| 2005/0159353 | A1 | 7/2005 | Veronese et al. |
| 2006/0182711 | A1 | 8/2006 | Bossard et al. |
| 2006/0239961 | A1 | 10/2006 | Bentley et al. |
| 2007/0092486 | A1* | 4/2007 | Yesland .................... 424/85.1 |
| 2010/0160610 | A1* | 6/2010 | Bossard et al. ............. 530/380 |

FOREIGN PATENT DOCUMENTS

| EP | 0267678 A1 | 5/1988 |
| EP | 0148605 B1 | 7/1990 |
| EP | 0205564 B1 | 5/1991 |
| EP | 0411678 B1 | 1/1992 |
| EP | 0209539 B1 | 5/1992 |
| EP | 0513738 A2 | 5/1992 |
| EP | 0248656 B1 | 3/1993 |
| EP | 0307247 B1 | 8/1994 |
| EP | 0343635 B1 | 8/1994 |
| EP | 0481791 B1 | 8/2003 |
| EP | 1333036 | 8/2003 |
| JP | 2005-509609 | 4/2005 |
| WO | WO 88/00967 A1 | 8/1987 |
| WO | WO 90/12874 A2 | 11/1990 |
| WO | WO 94/28024 A2 | 12/1994 |

(Continued)

OTHER PUBLICATIONS

Felix, "Site-Specific Poly(ethylene glycol)ylation of Peptides," American Chemical Society, Chapter 16, pp. 218-238, 1997.
Long et al., "Design of Homogeneous, Monopegylated Erythropoietin Analogs With Preserved In Vitro Bioactivity," Experimental Hematology, vol. 34, pp. 697-704, 2006.
Abuchowski, A. et al., "Alteration of Immunological Properties of Bovine Serum Albumin by Covalent Attachment of Polyethylene Glycol," *J. Biol. Chem.*, 1977, vol. 252. No. 11, pp. 3578-3581.
Abuchowski, A. et al., "Cancer Therapy with Chemically Modified Enzymes. I. Antitumor Properties of Polyethylene Glycol-Asparaginase Conjugates," *Cancer Biochem. Biophys.*, 1984, vol. 7, No. 2, pp. 175-186.
Annable, et al., "The Second International Reference Preparation of Erythropoietin, Human, Urinary, for Bioassay" *Bull. World Health Organ.*, 1972, vol. 47, No. 1. pp. 99-112.
Bavister, B., "Substitution of a Synthetic Polymer for Protein in a Mammalian Gamete Culture System," *J Exp Zool.*, 1981. vol. 271, No. 1, p. 45-51.

(Continued)

*Primary Examiner* — Elizabeth C Kemmerer
*Assistant Examiner* — Regina M Deberry
(74) *Attorney, Agent, or Firm* — King & Spalding LLP

(57) ABSTRACT

This invention relates to novel protein conjugates, in particular, to novel pegylated proteins, and their methods of making and use. One aspect of the present invention relates to pegylated-erythropoietin having greater clinical efficacy and stability during shipment and storage than current erythropoietin formulations.

18 Claims, 12 Drawing Sheets

(56) References Cited

FOREIGN PATENT DOCUMENTS

Figure 4A:
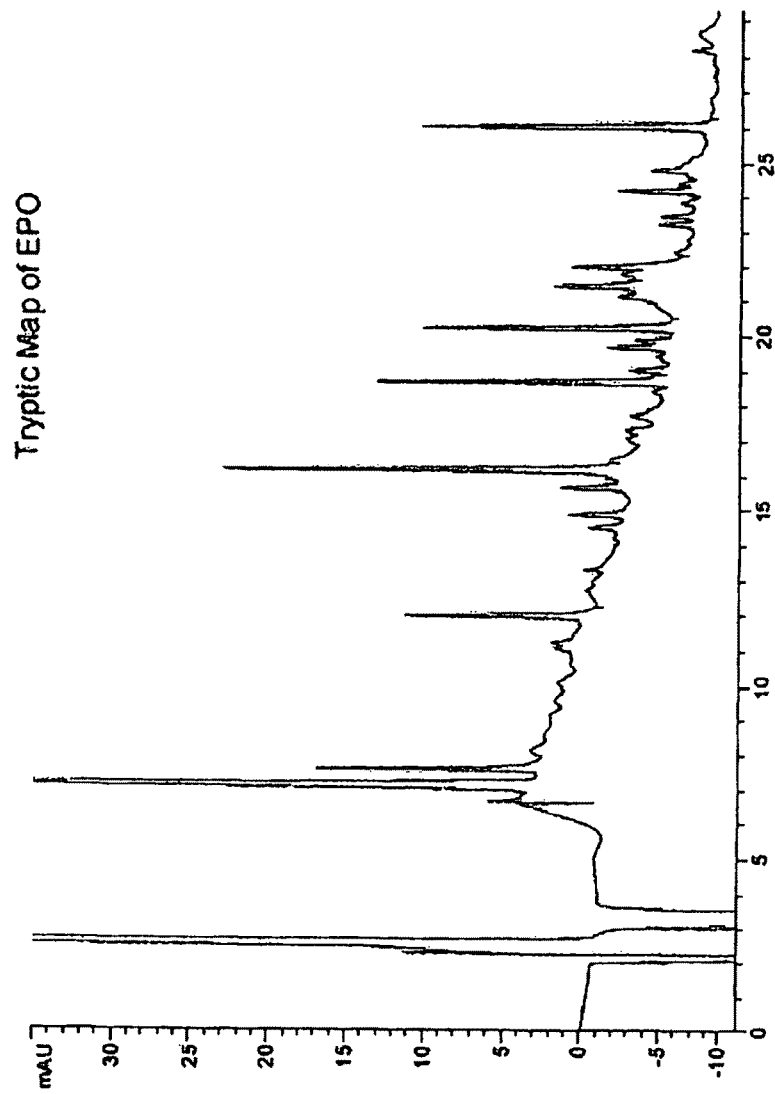

| WO | WO 96/35718 A1 | 11/1996 |
|---|---|---|
| WO | WO 97/09996 A1 | 3/1997 |
| WO | WO 97/40850 A1 | 11/1997 |
| WO | WO 98/58660 A1 | 12/1998 |
| WO | WO 99/07401 A2 | 2/1999 |
| WO | WO 01/02017 A2 | 1/2001 |
| WO | WO 02/32957 | 4/2002 |
| WO | WO 02/49673 | 6/2002 |
| WO | WO 03/029291 A2 | 4/2003 |
| WO | WO 03/055526 A2 | 7/2003 |
| WO | WO 03/070805 A1 | 8/2003 |
| WO | WO 2004/009627 A1 | 1/2004 |
| WO | WO 2004/056852 A2 | 7/2004 |
| WO | WO 2004/060406 A2 | 7/2004 |
| WO | WO 2004/091494 | 10/2004 |
| WO | WO2004/108667 | 12/2004 |
| WO | WO 2005/000360 A1 | 1/2005 |
| WO | WO 2005/010075 A2 | 2/2005 |
| WO | WO 2005/047366 A1 | 5/2005 |
| WO | WO 2005/053749 | 6/2005 |
| WO | WO 2005/089805 A2 | 9/2005 |
| WO | WO 2006/005058 A2 | 1/2006 |
| WO | WO 2006/019950 A2 | 2/2006 |
| WO | WO 2006/089228 A2 | 8/2006 |
| WO | WO 2006/110776 A2 | 10/2006 |
| WO | WO 2007/019331 A2 | 2/2007 |
| WO | WO 2011/041376 | 4/2011 |

OTHER PUBLICATIONS

Beauchamp, C. et al., "A New Procedure for the Synthesis of Polyethylene Glycol-Protein Adducts; Effects on Function, Receptor Recognition, and Clearance of Superoxide Dismutase. Lactoferrin, and Alpha 2-Macroglobulin," *Anal Biochem.*, 1983, vol. 131, No. 1, pp. 25-33.

Carnot, P. et al., "L'activite Hemopoietique de Serum au Cours de la Regeneration du Sang;" *C.R. Acad. Sci.*, 1906, vol. 143, pp. 432-437.

Chen, R. et al., Properties of Two Urate Oxidases Modified by the Covalent Attachment of Poly(Ethylene Glycol), *Biochim. Biophys Acta*, 1981, vol. 660. No. 2, pp. 293-298.

Danna, R. et al., "Erythropoietin Therapy for the Anemia Associated with AIDS and AIDS Therapy and Cancer," *Erythropoietin in Clinical Applications—An International Perspective*, 1990, pp. 301-324.

Egrie, "Pharmacokinetics of Recombinant Human Erythropoietin (rHuEpo) Administered to Hemodialysis," *Kidney Intl.*. 1988, vol. 33, p. 262. (abstract only available).

Egrie, J. et al., "Characterization and Biological Effects of Recombinant Human Erythropoietin," *Immunobiology*, 1986, vol. 172, No. 3-5. pp. 213-224.

Erslev, A. et al., "Humoral Regulation of Red Cell Production." *Blood*, 1953, vol. 8, pp. 349-357.

Eschbach, J. et al., "Recombinant Human Erythropoietin in Anemic Patients with End-Stage Renal Disease: Results of a Phase III Multicenter Clinical Trial," *Annals of Internal Medicine*, 1989, vol. III, pp. 992-1000.

Eschbach, J. et al.. "Correction of the Anemia of End-Stage Renal Disease with Recombinant Human Erythropoietin. Results of a Combined Phase I and II Clinical Trial," *N Engl J Med.*, 1987, vol. 316, No. 2, pp. 73-78.

Felix, A. et al., "Pegylated Peptides. IV. Enhanced Biological Activity of Site-Directed Pegylated GRF Analogs," *Int. J. Peptide Protein Res.*, 1995, vol. 46, No. 3-4, pp. 253-264.

Gaertner, H. et al., "Chemo-enzymic Backbone Engineering of Proteins," *J. Biol. Chem.*, 1994, vol. 269, No. 10, pp. 7224-7230.

Goodson, R. et al., "Site-Directed Pegylation of Recombinant Interleukin-2 at Its Glycosylation Site," *Biotechnology*, 1990, vol. 8, No. 4, pp. 343-346.

Jacobson, L. et al., "Role of the Kidney in Erythropoiesis," *Nature*, 1957, vol. 179, No. 4560, pp. 633-634.

Kawamoto, T. et al., "Development of a Serum-Free Medium for Growth of NS-1 Mouse Myeloma Cells and Its Application to the Isolation of NS-I Hybridomas," *Analytical Biochem.*, 1983, vol. 130, No. 2, pp. 445-453.

Kita, Y. et al., "Characterization of a Polyethylene Glycol Conjugate of Recombinant Human Interferon-Gamma," *Drug Des. Delivery*, 1990. vol. 6, No. 3, pp. 157-167.

Knauf M. et al., "Relationship of Effective Molecular Size to Systemic Clearance in Rats of Recombinant Interleukin-2 Chemically Modified with Water-Soluble Polymers." *J. Biol. Chem.*, 1988, vol. 263, No. 29, pp. 15064-15070.

Kovar, J. et al., "Serum-Free Medium for Hybridoma and Parental Myeloma Cell Cultivation," *Methods in Enzymology*, 1986, vol. 121, pp. 277-292.

Krantz, B., "Erythropoietin," *Blood*, 1991, vol. 77, No. 3, pp. 419-434.

Lai, P. et al., "Structural Characterization of Human Erythropoietin," *J. Biol. Chem.*, 1986, vol. 261, No. 7, pp. 3116-3121.

Lee-Huang, S., "Cloning and Expression of Human Erythropoietin cDNA in *Escherichia coli*," *Proc. Natl. Acad. Sci.* 1984, vol. 81, pp. 2708-2712.

Lim, V. et al., "Recombinant Human Erythropoietin Treatment in Pre-Dialysis Patients. A Double-Blind Placebo-Controlled Trial," *Ann. Intern. Med.*, 1989, vol. 110, No. 2, pp. 108-114.

Imal. N. et al., "Physicochemical and Biological Comparison of Recombinant Human Erythropoietin with Human Urinary Erythropoietin," *J. Biochem.*, 1990, vol. 107, No. 3, pp. 352-359.

Pearson et al., "Improved Tools for Biological Sequence Comparison," *Proc. Natl. Acad. Sci.*, 1988, vol. 85, No. 8, pp. 2444-2448.

Reissmann, K., "Studies on the Mechanism of Erythropoietic Stimulation in Parabiotic Rats During Hypoxia," *Blood*, 1950, vol. 5, pp. 372-380.

Rose, K. et al., "Preparation of Well-Defined Protein Conjugates Using Enzyme-Assisted Reverse Proteolysis" *Bioconjugate Chemistry*. 1991, vol. 2, pp. 154-159.

Sasaki, H. et al., "Carbohydrate Structure of Erythropoietin Expressed in Chinese Hamster Ovary Cells by a Human Erythropoietin cDNA," *J. Biol. Chem.*, 1987, vol. 262, No. 25, p. 12059-12076.

Schwarz, A. et al., "Enzymatic C-Terminal Biotinylation of Proteins," *Methods Enzymol.*, 1990, vol. 184, pp. 160-162.

Tsutsumi, Y. et al., "Polyethylene Glycol Modification of Interleukin-6 Enhances its Thrombopoietic Activity," *J. Controlled Release*, 1995, vol. 33, pp. 447-451.

Urrutiogoity, M. et al., "Biocatalysis in Organic Solvents with a Polymer-Bound Horseradish Peroxidase," *Biocatalysis*, 1989, vol. 2. pp. 145-149.

Zalipsky, S. et al., "Peptide Attachment to Extemities of Liposomal Surface Grafted PEG Chains: Preparation of the Long-Circulating Form of Laminin Pentapeptide, YIGSR." *Bioconjugate Chemistry*. 1995, vol. 6, No. 6, pp. 705-708.

* cited by examiner

```
Ala Pro Pro Arg Leu Ile Cys Asp Ser Arg Val Leu Glu
Arg Tyr Leu Leu Glu Ala Lys Glu Ala Glu Asn Ile Thr
Thr Gly Cys Ala Glu His Cys Ser Leu Asn Glu Asn Ile
Thr Val Pro Asp Thr Lys Val Asn Phe Tyr Ala Trp Lys
Arg Met Glu Val Gly Gln Gln Ala Val Glu Val Trp Gln
Gly Leu Ala Leu Leu Ser Glu Ala Val Leu Arg Gly Gln
Ala Leu Leu Val Asn Ser Ser Gln Pro Trp Glu Pro Leu
Gln Leu His Val Asp Lys Ala Val Ser Gly Leu Arg Ser
Leu Thr Thr Leu Leu Arg Ala Leu Gly Ala Gln Lys Glu
Ala Ile Ser Pro Pro Asp Ala Ala Ser Ala Ala Pro Leu
Arg Thr Ile Thr Ala Asp Thr Phe Arg Lys Leu Phe Arg
Val Tyr Ser Asn Phe Leu Arg Gly Lys Leu Lys Leu Tyr
Thr Gly Glu Ala Cys Arg Thr Gly Asp (SEQ ID NO:1)
```

FIG. 1

```
Ala Pro Pro Arg Leu Ile Cys Asp Ser Arg Val Leu Glu
Arg Tyr Leu Leu Glu Ala Lys Glu Ala Glu Asn Ile Thr
Thr Gly Cys Ala Glu His Cys Ser Leu Asn Glu Asn Ile
Thr Val Pro Asp Thr Lys Val Asn Phe Tyr Ala Trp Lys
Arg Met Glu Val Gly Gln Gln Ala Val Glu Val Trp Gln
Gly Leu Ala Leu Leu Ser Glu Ala Val Leu Arg Gly Gln
Ala Leu Leu Val Asn Ser Ser Gln Pro Trp Glu Pro Leu
Gln Leu His Val Asp Lys Ala Val Ser Gly Leu Arg Ser
Leu Thr Thr Leu Leu Arg Ala Leu Gly Ala Gln Lys Glu
Ala Ile Ser Pro Pro Asp Ala Ala Ser Ala Ala Pro Leu
Arg Thr Ile Thr Ala Asp Thr Phe Arg Lys Leu Phe Arg
Val Tyr Ser Asn Phe Leu Arg Gly Lys Leu Lys Leu Tyr
Thr Gly Glu Ala Cys Arg Thr Gly Asp Arg
(SEQ ID NO:2)
```

FIG. 2

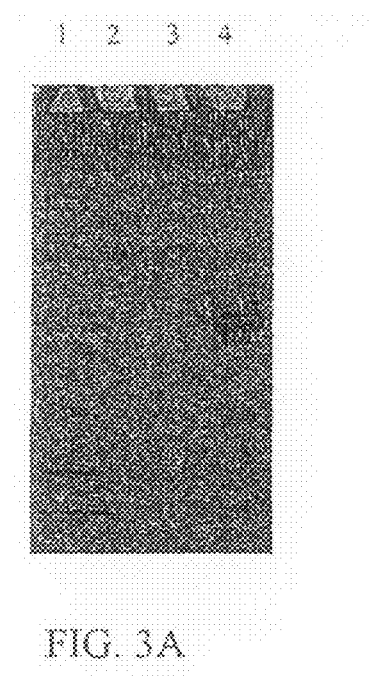
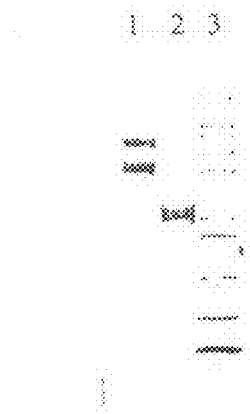
FIG. 3A
FIG. 3B

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

```
Pro Leu Arg Thr Ile Thr Ala Asp Thr Phe Arg Lys Leu Phe Arg Val
    130             135                 140

Tyr Ser Asn Phe Leu Arg Gly Lys Leu Lys Leu Tyr Thr Gly Glu Ala
145                 150             155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130             135                 140

Tyr Ser Asn Phe Leu Arg Gly Lys Leu Lys Leu Tyr Thr Gly Glu Ala
145                 150             155                 160

Cys Arg Thr Gly Asp Arg
                165
```

MODIFIED ERYTHROPOIETIN

CROSS REFERENCE TO RELATED APPLICATIONS

This application claims benefit of U.S. Provisional Application Ser. No. 60/835,429, filed Aug. 4, 2006, the entire contents of which are incorporated herein by reference for all purposes.

1. FIELD OF THE INVENTION

This invention relates to novel protein conjugates, in particular, to novel pegylated proteins, and their methods of making and use. One aspect of the present invention relates to pegylated-erythropoietin having greater clinical efficacy and stability during shipment and storage than current erythropoietin formulations.

2. BACKGROUND

In recent years, non-antigenic water-soluble polymers, such as polyethylene glycol ("PEG"), have been used for the covalent modification of polypeptides of therapeutic and diagnostic importance. PEG is a polymer that is nontoxic, nonimmunogenic, highly water soluble, and readily cleared from the body. PEG has many applications and is commonly used in foods, cosmetics, beverages, and prescription medicines. Pharmaceutical grade PEGs are approved for use in the United States by the FDA and are widely used as biopharmaceutical carriers, given their high degree of biocompatibility. PEGylation can modify certain characteristics of biopharmaceuticals without altering their function, thereby enhancing the therapeutic effect.

Generally, polyethylene glycol molecules are connected to the protein via a reactive group found on the protein. Amino groups, such as those on lysine residues or at the N-terminus, are convenient for such attachment. PEG can be coupled to active biopharmaceuticals through the hydroxyl groups at the ends of the chain using a variety of chemical methods. For example, covalent attachment of PEG to therapeutic polypeptides such as interleukins (Knauf, M. J. et al., J. Biol. Chem. 1988, 263, 15,064; Tsutsumi, Y. et al., J. Controlled Release 1995, 33, 447), interferons (Kita, Y. et al., Drug Des. Delivery 1990, 6, 157), catalase (Abuchowski, A. et al., J. Biol. Chem. 1977, 252, 3, 582), superoxide dismutase (Beauchamp, C. O. et al., Anal. Biochem. 1983, 131, 25), and adenosine deaminase (Chen, R. et al., Biochim. Biophy. Acta 1981, 660, 293), has been reported to extend their half life in vivo, and/or reduce their immunogenicity and antigenicity.

PEG molecules have been attached through amino groups on polypeptides using methoxylated PEG ("mPEG") having different reactive moieties. Such polymers include mPEG-succinimidyl succinate, mPEG-succinimidyl carbonate, mPEG-imidate, and mPEG-cyanuric chloride. Alternatively, site-specific pegylation at the N-terminus, side chain and C-terminus of a potent analog of growth hormone-releasing factor has been performed through solid-phase synthesis (Felix, A. M. et al., Int. J. Peptide Protein Res. 1995, 46, 253). Site specific pegylation at the N-terminus has also been performed using aldehyde-activated PEG; however such reactions require long reaction times and are heavily dependent on pH. For example, the reaction requires from 18 to 36 hours and is generally specific only at acidic pH, becoming random at neural or higher pH (see e.g., U.S. Pat. Nos. 6,077,939 and 5,985,265, each of which is hereby incorporated by reference in its entirety). This limits the available peptides to those that can withstand prolonged acidic conditions.

An additional method used involved attaching a peptide to extremities of liposomal surface-grafted PEG chains in a site-specific manner through a reactive aldehyde group at the N-terminus generated by sodium periodate oxidation of N-terminal threonine (Zalipsky, S. et al., Bioconj. Chem. 1995, 6, 705). However, this method is limited to polypeptides with N-terminal serine or threonine residues.

Enzyme-assisted methods for introducing activated groups specifically at the C-terminus of a polypeptide have also been described (Schwarz, A. et al., Methods Enzymol. 1990, 184, 160; Rose, K. et al., Bioconjugate Chem. 1991, 2, 154; Gaertner, H. F. et al., J. Biol. Chem. 1994, 269, 7224). Typically, these active groups can be hydrazide, aldehyde, and aromatic-amino groups for subsequent attachment of functional probes to polypeptides.

Site-specific mutagenesis is a further approach which has been used to prepare polypeptides for site-specific polymer attachment. WO 90/12874 describes the site-directed pegylation of proteins modified by the insertion of cysteine residues or the substitution of other residues for cysteine residues. This publication also describes the preparation of mPEG-erythropoietin ("mPEG-EPO") by reacting a cysteine-specific mPEG derivative with a recombinantly introduced cysteine residue on EPO. Similarly, interleukin-2 was pegylated at its glycosylation site after site-directed mutagenesis (Goodson, R. J. et al., Bio/Technology 1990, 8, 343).

Glycoproteins provide carbohydrates as additional target sites for modification. The enzyme peroxidase has been modified with PEG-diamine through its carbohydrate moiety (Urrutiogoity, M. et al., Biocatalysis 1989, 2, 145). WO 94/28024 describes the methods for preparing mPEG-EPO through periodate-oxidized carbohydrate. The chemistry involved was hydrazone formation by reacting mPEG-hydrazide with aldehyde groups of the carbohydrate moiety on EPO. This type of modification generates reactive aldehyde groups through an oxidation step, which potentially can oxidize various types of sugar residues in the carbohydrate moiety and some amino acid residues in the polypeptide, such as methionine.

Erythropoietin

An exemplary protein that demonstrates the need for improved pegylation methods is erythropoietin. Erythropoiesis is the production of red blood cells, which occurs to offset cell destruction. Erythropoiesis is a controlled physiological mechanism that enables sufficient red blood cells to be available for proper tissue oxygenation. Naturally occurring human erythropoietin (hEPO) is a polypeptide produced in the kidney and is the humoral plasma factor which stimulates red blood cell production (Carnot, P and Deflandre, C (1906) C.R. Acad. Sci. 143: 432; Erslev, A J (1953 Blood 8: 349; Reissmann, K R (1950) Blood 5: 372; Jacobson, L 0, Goldwasser, E, Freid, W and Plzak, L F (1957) Nature 179: 6331-4). Naturally occurring EPO stimulates the division and differentiation of committed erythroid progenitors in the bone marrow and exerts its biological activity by binding to receptors on erythroid precursors (Krantz, B S (1991) Blood 77: 419).

Erythropoietin has been manufactured biosynthetically using recombinant DNA technology (Egrie, J C, Strickland, T W, Lane, J et al. (1986) Immunobiol. 72: 213-224) and is the product of a cloned human EPO gene inserted into and expressed in the ovarian tissue cells of the Chinese hamster (CHO cells). The primary structure of the predominant, fully processed form of hEPO is illustrated in SEQ ID NO:1. There are two disulfide bridges between $Cys^7$-$Cys^{161}$ and $Cys^{29}$-

Cys$^{33}$. The molecular weight of the polypeptide chain of EPO without sugar moieties is 18,236 Da. In the intact EPO molecule (molecular weight of about 33 kD), approximately 40% of the molecular weight is accounted for by the carbohydrate groups that glycosylate the protein at glycosylation sites on the protein (Sasaki, H, Bothner, B, Dell, A and Fukuda, M (1987) J. Biol. Chem. 262: 12059).

Because human erythropoietin is essential in red blood cell formation, the hormone is useful in the treatment of blood disorders characterized by low or defective red blood cell production and other diseases for which expansion of red blood cell production would be beneficial to the patient. For example, EPO has been used in the treatment of anemia in chronic renal failure patients (CRF) (Eschbach, J W, Egri, J C, Downing, M R et al. (1987) NEJM 316: 73-78; Eschbach, J W, Abdulhadi, M H, Browne, J K et al. (1989) Ann. Intern. Med. 111: 992; Egrie, J C, Eschbach, J W, McGuire, T, Adamson, J W (1988) Kidney Intl. 33: 262; Lim, V S, Degowin, R L, Zavala, D et al. (1989) Ann. Intern. Med. 110: 108-114) and in AIDS and cancer patients undergoing chemotherapy (Danna, R P, Rudnick, S A, Abels, R I In: M B, Garnick, ed. Erythropoietin in Clinical Applications—An International Perspective. New York, N.Y.: Marcel Dekker; 1990: p. 301-324).

However, the bioavailability of commercially available protein therapeutics such as EPO is limited by their short plasma half-life and susceptibility to protease degradation. These shortcomings prevent them from attaining maximum clinical potency and generally require more frequent treatments or administration of greater amounts of drug which can result in increased frequency and severity of side effects and lack of patient compliance with the treatment schedule. Proteins, including native EPO and its derivatized and modified forms, are also generally formulated with albumin (HSA or serum), and stored and transported at reduced temperature to help maintain product stability through use. HSA serum-containing formulations are undesirable because of the risk of contamination by human infectious agents and the high costs associated with pharmaceutical grade HSA and related bioassays.

ARANESP® (darbepoietin alfa) is a commercially available EPO derivative. It is a 165-amino acid protein that differs from recombinant human erythropoietin in containing 5 N-linked oligosaccharide chains, whereas recombinant human erythropoietin contains 3 chains. The two additional N-glycosylation sites result from amino acid substitutions in the erythropoietin peptide backbone. The additional carbohydrate chains increase the approximate molecular weight of the glycoprotein from 30,000 to 37,000 daltons. ARANESP® is supplied in two formulations with different excipients, one containing polysorbate 80 and another containing albumin (HSA), a derivative of human blood.

Pegylated proteins, e.g., EPO derivatives, have been disclosed (U.S. Publication Nos. 2002/0115833, 2003/0120045 and 2003/0166566) However, the processes used to make these compositions are difficult to implement and control, costly, use toxic compounds in the synthesis, or have other quality control problems. Moreover, they are not known to generate polypeptide conjugates that have biological activity greater than natural function of the unmodified polypeptide.

As such, there remains an acute need for a pegylated composition, and/or method of production thereof, that is easier and less costly to implement and, most importantly, easier to control in order to produce a predictable and consistent product.

With particular respect to EPO, formulations are required that have improved plasma half-lives, increased activity, and decreased susceptibility to protease degradation relative to currently available formulations. Moreover, such formulations should optimally be able to be packaged, shipped, and stored in protein-free formulations and/or under standard conditions.

All scientific publications including patent documents cited herein are incorporated by reference in their entirety for all purposes.

3. SUMMARY OF THE INVENTION

The present invention is based on the surprising discovery of novel forms of mono- and di-pegylated proteins, e.g., erythropoietin ("EPO"), and mixtures thereof. As demonstrated using EPO, the formulations of the invention exhibit improved in vivo activity, including improved plasma half-lives and stability, relative to recombinant human EPO and/or other commercially available EPO therapeutics. The EPO molecules and compositions of the invention further exhibit prolonged stability in protein-free formulations and/or remain stable under standard storage conditions, i.e., storage at standard temperature, e.g., about 25° C.

In certain embodiments, the invention relates to a pharmaceutical formulation comprising at least one population of erythropoietin proteins wherein each erythropoietin protein is covalently linked to at least one polyethylene glycol molecule; and a protein free pharmaceutical carrier. In a specific embodiment, each erythropoietin protein is covalently linked to one polyethylene glycol molecule. In another embodiment, each erythropoietin protein is linked to two polyethylene glycol molecules. In a further embodiment, the at least one population of erythropoietin proteins is a first and a second population, wherein the first population of erythropoietin proteins is linked to one polyethylene glycol molecule and the second population is linked to two polyethylene glycol molecules. In yet another embodiment, the ratio of the first to the second population can range from less than about 1 to about 100, about 10 to about 90, about 20 to about 80, about 30 to about 70, about 40 to about 60, about 50 to about 50, about 60 to about 40, about 70 to about 30, about 80 to about 20, about 90 to about 10, or about 100 to less than about 1, wherein less than about 1 includes an amount undetectable using standard methods known in the art.

In yet a further embodiment, each erythropoietin protein is covalently linked to at least one polyethylene glycol molecule through a particular lysine residue. In certain embodiments, the invention comprises a composition having at least one erythropoietin molecule covalently linked to at least one polyethylene glycol molecule via the amino terminus of the erythropoietin protein, which covalent linkage is not through an aldehyde linkage. In other embodiments, the invention comprises a composition having at least one erythropoietin molecule covalently linked to at least one polyethylene glycol molecule through a particular lysine residue, which residue is lysine 116. In still another embodiment, the formulation may be capable of storage for an extended period of time without substantial degradation of erythropoietin in a carrier-protein free formulation.

The present invention also relates to methods of manufacture and use of novel forms of pegylated proteins, e.g., EPO, in particular, for use in pharmaceutical formulations. Using the methods of production provided herein, the pegylated protein of the invention is a conjugate, wherein the protein is covalently linked to at least one polyethylene glycol molecule. In a specific embodiment, the pegylated protein of the invention is an EPO molecule that is covalently linked to one or two PEG molecules. In one embodiment of this aspect of the invention, the covalent link is by way of the amino terminus of the protein. In another embodiment of this aspect of the invention, the covalent link is via a lysine residue of the EPO protein, e.g., lysine 116. Accordingly, the pegylated proteins of the invention encompass proteins covalently conjugated to at least one polyethylene glycol molecule. In a specific embodiment, the invention encompasses EPO protein covalently conjugated to one or two polyethylene glycol molecules (i.e., mono- or di-pegylated-EPO, respectively), and/or mixtures thereof. In certain embodiments, the pegylated protein conjugates of the invention encompass mono-pegylated protein. The mono-pegylated protein of the invention may be uniform in that for each conjugate, the polyethelyene glycol ("PEG") molecule is covalently attached to the protein via the same amino acid residue. In other embodiments, the mono-pegylated protein of the invention comprises a plurality of conjugates in that, for each conjugate, the single PEG molecule is conjugated to the EPO protein via a differing amino acid residue or the N-terminus of the protein (i.e., the α-amino group of the protein), wherein the said amino acid residue is one of the amino acid residues suitable for covalent conjugation to PEG as described herein. In still other embodiments, the pegylated protein conjugates of the invention encompass proteins having multiple sites of pegylation, e.g., di-pegylated proteins. The multiple-pegylated proteins of the invention may be uniform in that for each conjugate, the two or more PEG molecules are covalently attached to each protein at the same sites. In other embodiments, the multiple-pegylated protein of the invention comprises a plurality of conjugates in that, for each conjugate, the two or more PEG molecules are conjugated to the protein at any two or more of the available amino acid residues suitable for covalent conjugation to PEG as described herein and/or the amino terminus of the protein. For example, in specific embodiments, EPO conjugates of the invention comprise a plurality of mono- and di-pegylated EPO, wherein the site(s) of the conjugation between the EPO protein and the PEG molecule(s) is(are) non-uniform.

Accordingly, in a specific embodiment, the methods of production presented herein produce a composition that encompasses a plurality of EPO conjugates, each conjugate comprising an EPO protein covalently linked to one or two PEG molecules, wherein the plurality comprises a conjugate having at least one of said one or two covalent linkages at the amino terminus of the protein, which covalent linkage at said amino terminus in not through an aldehyde linkage. In another embodiment, the invention encompasses a plurality of EPO conjugates, each conjugate comprising an EPO protein covalently linked to one or two PEG molecules, wherein the plurality comprises a conjugate having at least one of said one or two covalent linkages at the amino terminus of the protein, which covalent linkage at said amino terminus in not through an aldehyde linkage, and one or more of or all of: a conjugate having at least one of said one or two covalent linkages at lysine 116, a conjugate having at least one of said one or two covalent linkages at lysine 52 of the EPO protein, and/or a conjugate having at least one of said one or two covalent linkages at lysine 154 of the EPO protein. In other embodiments, the invention encompasses a plurality of EPO conjugates, each conjugate comprising an EPO protein covalently linked to one or two PEG molecules, wherein the plurality comprises a conjugate having at least one of said one or two covalent linkages at the amino terminus of the protein, which covalent linkage at said amino terminus in not through an aldehyde linkage, and a conjugate having said one or two covalent linkages at any site suitable for such linkage as described herein or known in the art.

In certain embodiments, the invention encompasses a plurality of EPO conjugates, each conjugate comprising an EPO protein covalently linked to one or two PEG molecules, wherein the plurality comprises a conjugate having at least one of said one or two covalent linkages at lysine 116. In another embodiment, the invention encompasses a plurality of EPO conjugates, each conjugate comprising an EPO protein covalently linked to one or two PEG molecules, wherein the plurality comprises a conjugate having at least one of said one or two covalent linkages at lysine 116, and one or more of or all of: a conjugate having at least one of said one or two covalent linkages at the amino terminus of the protein, which covalent linkage at said amino terminus in not through an aldehyde linkage, a conjugate having at least one of said one or two covalent linkages at lysine 52 of the EPO protein, a conjugate having at least one of said one or two covalent linkages at lysine 154 of the EPO protein. In another embodiment, the invention encompasses a plurality of EPO conjugates, each conjugate comprising an EPO protein covalently linked to one or two PEG molecules, wherein the plurality comprises a conjugate having at least one of said one or two covalent linkages at lysine 116 and a conjugate having said one or two covalent linkages at any site suitable for such linkage as described herein or known in the art.

In a specific embodiment, the invention encompasses a plurality of EPO conjugates, each conjugate comprising an EPO protein covalently linked to one or two PEG molecules, wherein said plurality comprises a mono-pegylated EPO having the PEG molecule covalently attached to the EPO protein via lysine 116. In another embodiment, the invention encompasses a plurality of EPO conjugates, each conjugate comprising an EPO protein covalently linked to one or two PEG molecules, wherein said plurality comprises a mono-pegylated EPO having the PEG molecule covalently attached to the EPO protein via lysine 116 and one or more of or all of: a conjugate having at least one of said one or two covalent linkages at the amino terminus of the EPO protein, which covalent linkage at said amino terminus in not through an aldehyde linkage, a conjugate having at least one of said one or two covalent linkages at lysine 52 of the EPO protein, and a conjugate having at least one of said one or two covalent linkages at lysine 154 of the EPO protein. In other embodiments, the invention encompasses a plurality of EPO conjugates, each conjugate comprising an EPO protein covalently linked to one or two PEG molecules, wherein said plurality comprises a mono-pegylated EPO having the PEG molecule covalently attached to the EPO protein via the amino terminus of the protein, which covalent linkage at said amino terminus in not through an aldehyde linkage. In another embodiment, the invention encompasses a plurality of EPO conjugates, each conjugate comprising an EPO protein covalently linked to one or two PEG molecules, wherein said plurality comprises a mono-pegylated EPO having the PEG molecule covalently attached to the EPO protein via the amino terminus of the protein, which covalent linkage at said amino terminus in not through an aldehyde linkage, and one or more of or all of: a conjugate having at least one of said one or two covalent linkages at lysine 116 of the EPO protein, a conjugate having at least one of said one or two covalent linkages at lysine 52 of the EPO protein, and a conjugate having at least one of said one or two covalent linkages at lysine 154 of the EPO protein. In certain other embodiments, the invention encompasses any of the foregoing plurality of EPO conjugates, further comprising a conjugate having said one or two covalent linkages at any site suitable for such linkage as described herein or known in the art.

In certain embodiments, the plurality of protein conjugates of the invention comprises at least one population of conjugates, wherein said at least one population comprises protein covalently linked to at least one PEG molecule. In other embodiments, the at least one population of protein conjugates is a first and a second population, wherein said first population is linked to one PEG molecule and the second population is linked to two or more PEG molecules. In certain embodiments, said covalent linkages include non-aldehyde linkages at the amino-terminus of the protein. In a specific embodiment, the at least one population of protein conjugates is an at least one population of EPO-conjugates that is a first and a second population, wherein said first population is EPO-PEG covalently linked to one PEG molecule and the second population of EPO-PEG is EPO protein covalently linked to two PEG molecules. In certain embodiments, the ratio of the first population to the second population can range from less than about 1 to about 100, about 10 to about 90, about 20 to about 80, about 30 to about 70, about 40 to about 60, about 50 to about 50, about 60 to about 40, about 70 to about 30, about 80 to about 20, about 90 to about 10, or about 100 to less than about 1, wherein less than about 1 includes an amount undetectable using standard methods known in the art.

The invention further encompasses a plurality of protein conjugates, each conjugate comprising an EPO protein covalently linked to at least one PEG molecule, wherein administration of said plurality to a subject results in a serum concentration of said plurality, or a serum concentration of one or more components of said plurality, of at least about 10%-700% greater than that obtainable by administration of an equivalent amount (e.g. based on protein concentration or activity units, e.g., EPO units) of a control formulation at about 24, 36 or 48 hours after injection. In a specific embodiment with respect to a plurality of EPO conjugates of the invention the control formulations may be, e.g., recombinant human EPO (rhuEPO), native EPO or a commercial EPO formulation, e.g., ARANESP® (darbopoietin alfa)). In a specific embodiment, administration (e.g., subcutaneously, intravenously) of the plurality of EPO conjugates of the invention into Sprague-Dawley rats results in a serum concentration of about at least 5% to 700% greater than that obtainable by administration of a control EPO formulation at about 16, 20, 24, 28, 32, 36, 40, 44, 48, 52, 56, 60, 64, 68 or 72 hours post administration. The invention encompasses any method of administration described herein and/or known in the art suitable for delivery of a therapeutic protein, e.g., a therapeutic pegylated protein, to a subject; such methods include, but are not limited to, intramuscular, parenteral, pulmonary, nasal and oral. The plurality of protein conjugates of the invention may also include various additional materials, including, in particular, any suitable pharmaceutically acceptable carrier described herein and/or known in the art for administration to a subject.

In another specific embodiment, the invention encompasses a plurality of EPO conjugates, each conjugate comprising an EPO protein covalently linked to one or two PEG molecules, wherein administration of said plurality to a subject results in an about at least 5%-250% greater increase in hematocrit that that obtainable by administration of an equivalent amount (e.g., based on EPO units) of a control EPO formulation (e.g., recombinant human EPO (rhuEPO), native EPO or a commercial EPO formulation, e.g., ARANESP® (darbopoietin alfa)) at about 5, 7, 10, 12, 14, 16, 18 or 21 days post administration. In a specific embodiment, administration (e.g., subcutaneously) of the plurality of EPO conjugates of the invention to Sprague-Dawley rats results in an about 5% greater to about 250% increase in hematocrit that that obtainable by administration of an equivalent amount (e.g., based on EPO units) of a control EPO formulation (e.g., recombinant human EPO (rhuEPO), native EPO or a commercial EPO formulation, e.g., ARANESP® (darbopoietin alfa)) at about 5, 7, 10, 12, 14, 16, 18 or 21 days post administration.

The invention further encompasses pharmaceutical formulations comprising a plurality of the protein conjugates described herein, and/or comprising one or more of the components of said plurality (e.g., a population of EPO conjugates covalently linked to one PEG molecule and/or a population of EPO conjugates covalently linked to two PEG molecules and/or a population of EPO conjugates covalently linked to one or two PEG molecules, wherein at least one of said one or two covalent linkages is at the amino terminus of the protein, which covalent linkage at said amino terminus in not through an aldehyde linkage), and a protein-free (e.g., serum-free, albumin-free, human serum albumin-free ("hsa-free")) pharmaceutically acceptable carrier. In certain embodiments, the pharmaceutical formulations of the invention comprising a protein-free pharmaceutically acceptable carrier may be stored for extended period of time without substantial and/or detectable degradation of erythropoietin as determined by methods described herein and/or known in the art. In certain embodiments, the pharmaceutical formulations of the invention are stable (i.e., do not exhibit detectable and/or do not exhibit substantial degradation) in such protein-free formulations as determined at least 15 months after storage at about $-20°$ C. or $4°$ C. In other embodiments, the pharmaceutical formulations of the invention are stable (i.e., do not exhibit detectable and/or do not exhibit substantial degradation) in such protein-free formulations as determined at least 10 months after storage at about $25°$ C. or about $37°$ C. The stability of pharmaceutical formulations of the invention may be assessed by any method known in the art and/or described herein. In certain embodiments, the stability of the pharmaceutical formulations of the invention is assessed by monitoring alteration in the protein concentration over time as determined by a bicinchoninic acid ("BCA") protein assay. In other embodiments, the stability of the pharmaceutical formulations of the invention is assessed by indication of protein degradation (i.e., EPO conjugate degradation) over time as determined by SDS PAGE analysis. In still other embodiments, the stability of the pharmaceutical formulations of the invention is assessed by monitoring the activity of said formulation over time, wherein said activity is determined by any in vitro or in vivo method known in the art for determination of activity of said formulation (e.g., an EPO formulation). In a specific example in accordance with this embodiment, the activity of a pharmaceutical formulation of the invention comprising a plurality of EPO-conjugates is evaluated by the ability of said pharmaceutical formulation to induce stem cell differentiation into erythroid cells in vitro.

Another aspect of the invention relates to a protein conjugate made by the method comprising, reacting a protein with an activated water-soluble polymer in a reaction buffer to covalently link the protein with the activated water-soluble polymer and removing substantially all unlinked water-soluble polymer to obtain said EPO conjugate. In preferred embodiments of this aspect of the invention, the activated water-soluble polymer is SC-PEG. In another embodiment, the activated water-soluble polymer is NHS-PEG. In preferred embodiments, the reaction buffer does not comprise aldehyde-PEG and/or the activated water-soluble polymer is not aldehyde-PEG. In certain embodiments, the reaction buffer has a pH of about 6.5 to about 8.5. In other embodiments, the reaction buffer has a pH of about 6.5 to about 7.5, about 6.6 to about 7.3, or about 6.7 to about 7.1. In preferred embodiments, the reaction buffer has a neutral pH of about 7.0. In certain embodiments, the reaction buffer may further comprise 5%-80% DMSO (v/v), and preferably comprises 10%-40% DMSO (v/v). The methods of the invention may allow lower amounts, i.e., lower concentrations, of PEG to be used in the reaction buffer relative to standard methods known in the art while improving or maintaining similar pegylation efficiencies (i.e., evaluated as amount of pegylated product relative to non-pegylated product) of said known methods. The methods of the invention may also allow the use of a reaction at a higher pH than other methods known in the art (e.g., pegylation of a protein using aldehyde PEG (see, e.g., U.S. Pat. Nos. 6,077,939 and 5,985,265, each of which is hereby incorporated by reference in its entirety). Such modifications relative to methods known in that art may provide manufacturing advantages in terms of costs, manufacturing efficiency, and/or ease of process. In yet a further embodiment, the reaction buffer comprises a molar ratio of protein to activated water-soluble polymer of about 1 to about 3 to about 1 to about 60. In other embodiments, the reaction buffer comprises a molar ratio of protein to activated water-soluble polymer of about 1 to about 4, about 1 to about 5, about 1 to about 6, about 1 to about 7, about 1 to about 8, about 1 to about 9, about 1 to about 10, about 1 to about 15, about 1 to about 20, about 1 to about 25, about 1 to about 30, about 1 to about 35, about 1 to about 40, about 1 to about 45, about 1 to about 50, about 1 to about 55, about 1 to about 60.

In certain embodiments, the reaction buffer comprises a molar ratio of protein to activated water-soluble polymer of about 1 to about 7. In still a further embodiment, the removing of substantially all unreacted water-soluble polymer can be accomplished routinely by methods known in the art (e.g., dialysis, chromatography).

Another aspect of the invention relates to treating a patient in need thereof with a pharmaceutically effective amount of aforementioned formulations or conjugates. In one embodiment, the present invention encompasses the use of compositions, in particular pharmaceutical compositions, comprising the plurality of EPO conjugates of the invention, or one or more components of said plurality, at therapeutically effective concentrations for increasing the red blood cell production in a subject in need thereof. In certain embodiments, the pharmaceutical compositions of the invention are administered to treat or manage a disease or disorder associated with aberrant or deficient red blood cell production, or to alleviate the symptoms thereof, in said subject. In certain embodiments, the subject to be treated has not been diagnosed with a disease or disorder associated with aberrant or deficient red blood cell production, but is determined to have a predisposition for developing said disease or disorder. In still other embodiments, the subject to be treated has not been diagnosed with a disease or disorder associated with aberrant or deficient red blood cell production, but is evaluated by standards of the art as obtaining benefit from said treatment. In certain embodiments, the patient receives a dose at least about once a week. In other embodiments, the patient receives a dose at least about once every two weeks, at least about once every three weeks, or at least about once every month.

Additional advantages of the present invention will become readily apparent to those skilled in this art from the following detailed description, wherein only the preferred embodiment of the invention is shown and described. As will be realized, the invention is capable of other and different embodiments, and its several details are capable of routine modifications in various respects, all without departing from the invention. The present invention may be practiced without some or all of these specific details. Accordingly, the drawings and description are to be regarded as illustrative in nature, and not as restrictive.

4. BRIEF DESCRIPTION OF THE DRAWINGS

FIG. 1. Amino acid sequence of the predominant, fully processed human erythropoietin ("hEPO") (SEQ ID NO:1).

FIG. 2. Amino acid sequence of erythropoietin, with terminal Arg residue (SEQ ID NO:2)

FIG. 3A-B. FIG. 3A: Lane 1 is molecular weight marker. Lane 2 is the sample after 5 months of storage at 4° C. in the formulation buffer. Lane 3 is the control of the sample stored in frozen state at −20° C. for 5 months, and lane 4 is the unmodified EPO. FIG. 3B Starting from the left side: Lane 1: Sample immediately after production. Lane 2: Native EPO, Lane 3: Molecular weight marker.

Figure 4B:
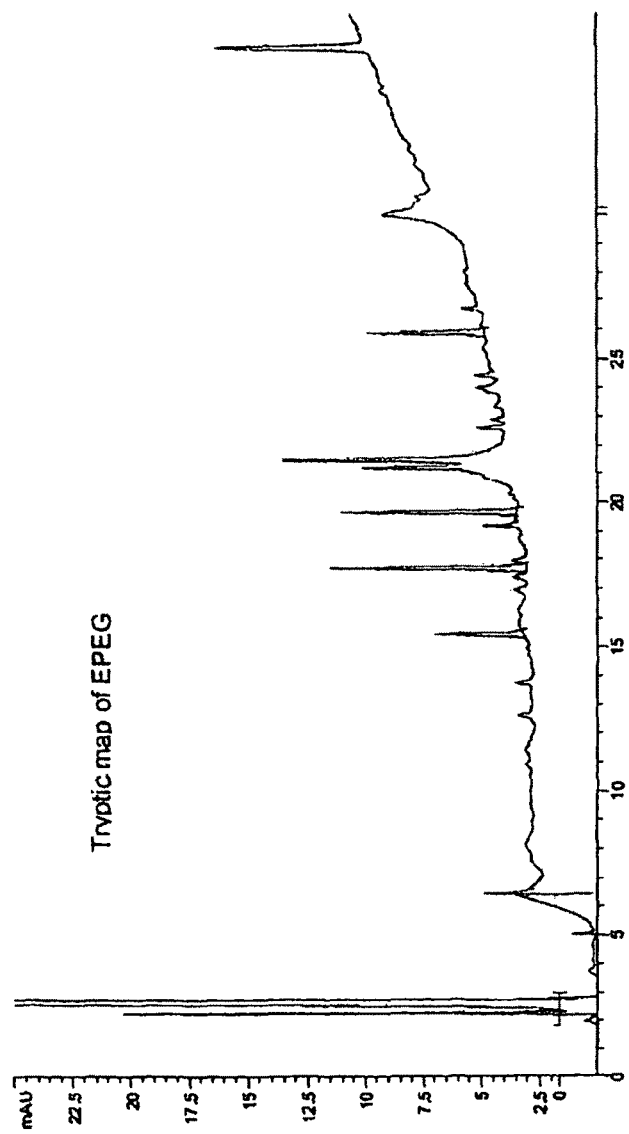

FIGS. 4A-B. A: Exemplary tryptic digestion of native EPO. B: Exemplary tryptic digestion of EPO conjugate prepared according to the Example 1.

Figure 5:
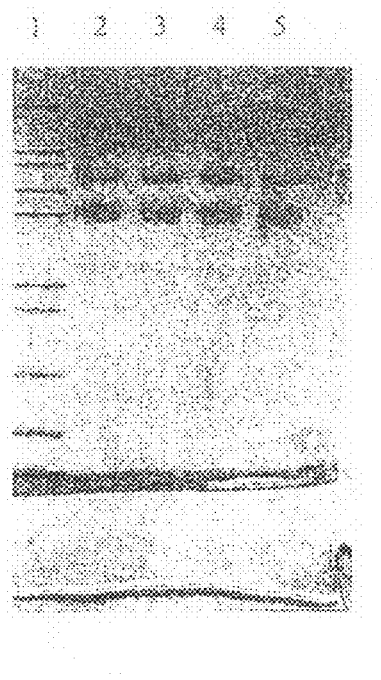

FIG. 5: SDS-PAGE analysis of EPEG conjugates stored at high temperatures for various period of time. Lane 1: molecular weight standard in kD (200, 116.3, 97.4, 66.3, 55.4, 36.5, 31, 21.5 and 14.4); lane 2: −20° C., 15 months; lane 3: 4° C., 16 months; lane 4: 25° C. 10.5 months; lane 5: 37° C., 10.5 months.

Figure 6:
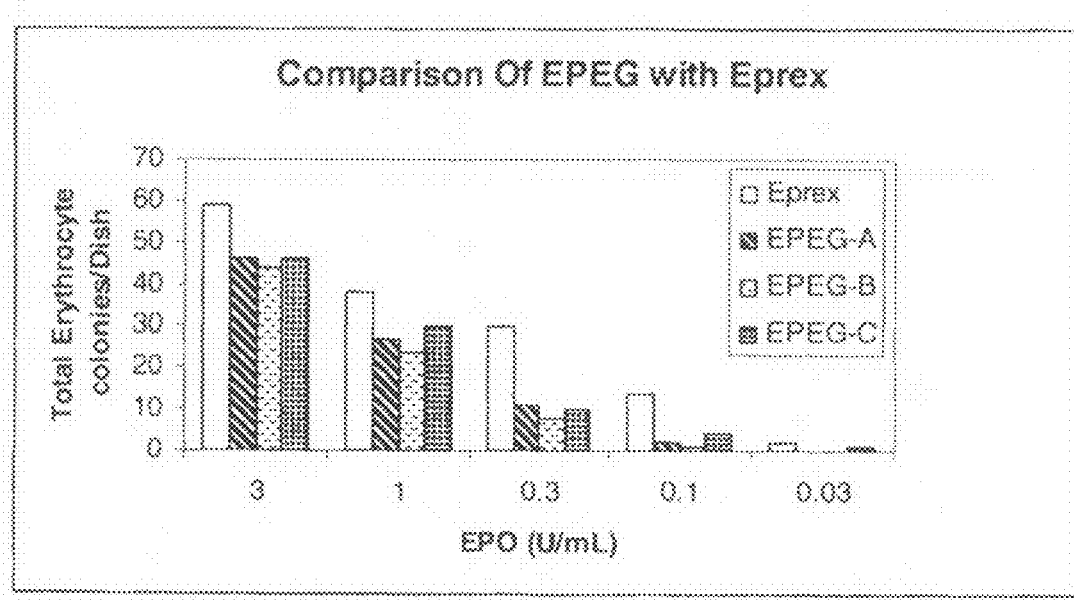

FIG. 6: Comparison of standard (EPREX® (epoetin alfa)) and EPO conjugate ('EPEG') activity on Erythroid Progenitor Proliferation in MethCult™-4230 (no Cytokine).

Figure 7:
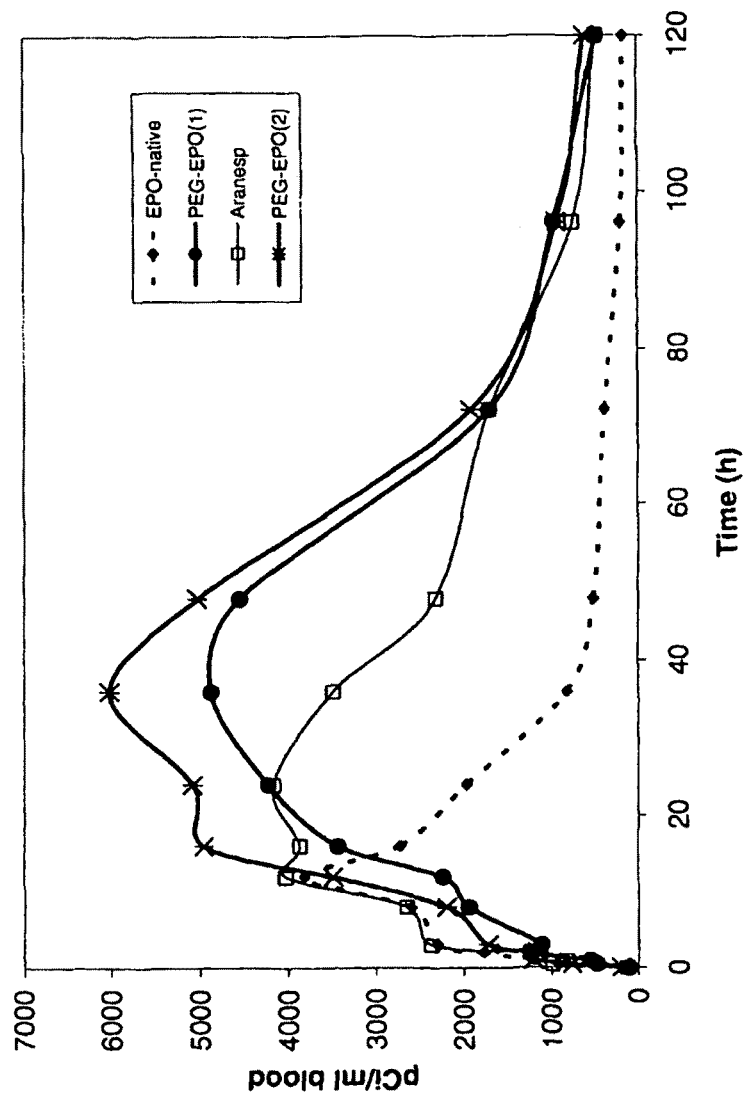

FIG. 7: Pharmacokinetics Profiles of EPO, EPEG and ARANESP® (darbopoietin alfa) on intravenous injection in male Sprague-Dawley rats.

Figure 8:
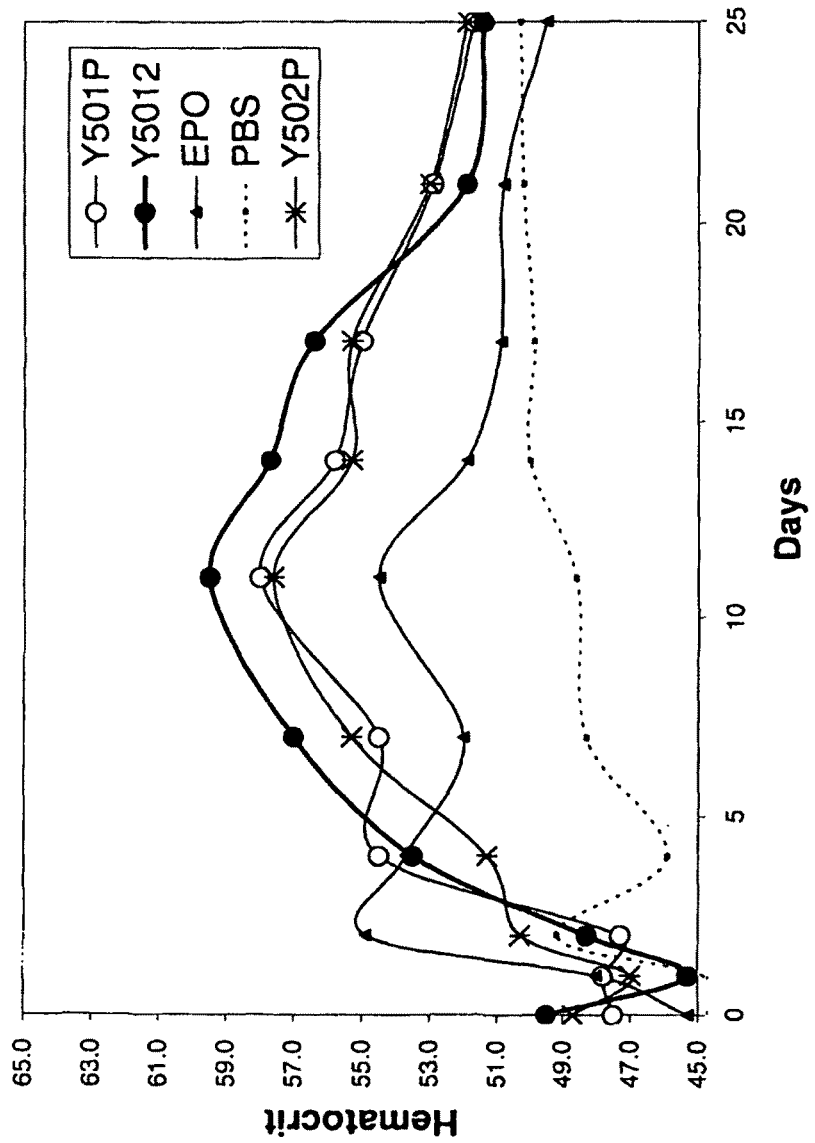

FIG. 8. Comparison of the in vivo activity of EPO conjugates of the invention. The hematocrit level over time of three PEG-EPO samples was compared with that of the native EPO at 5 µg/rat dosage. Y501 P: EPO modified by branched chain NHS-PEG (20,000 KD) having 1PEG-EPO. Y502P: EPO modified by branched chain NHS-PEG (20,000 KD) having 2PEG-EPO. Y5012: EPO modified by branched chain NHS-PEG (20,000 KD) having equal amounts of 1PEG-EPO and 2PEG-EPO.

Figure 9:
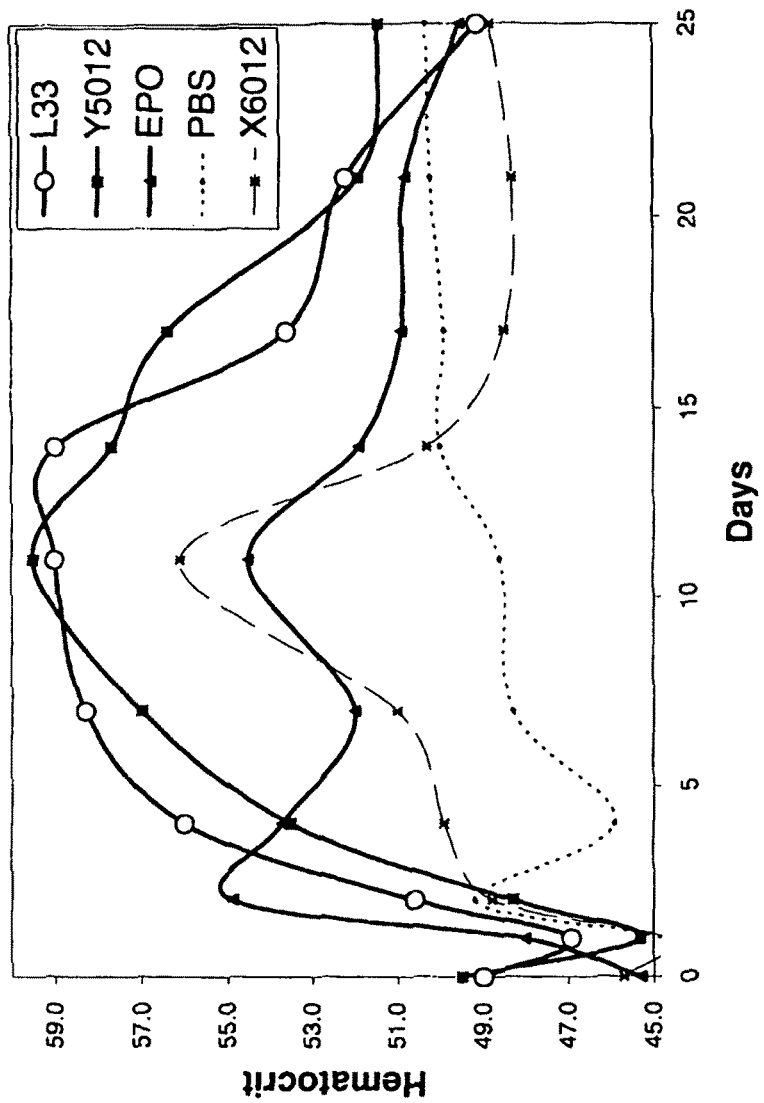

FIG. 9 Time course plot of comparison of 3 different EPEGs (L33, Y5012 and X6012) and native EPO for activity in induction of hematocrit increase in rats.

Figure 10:
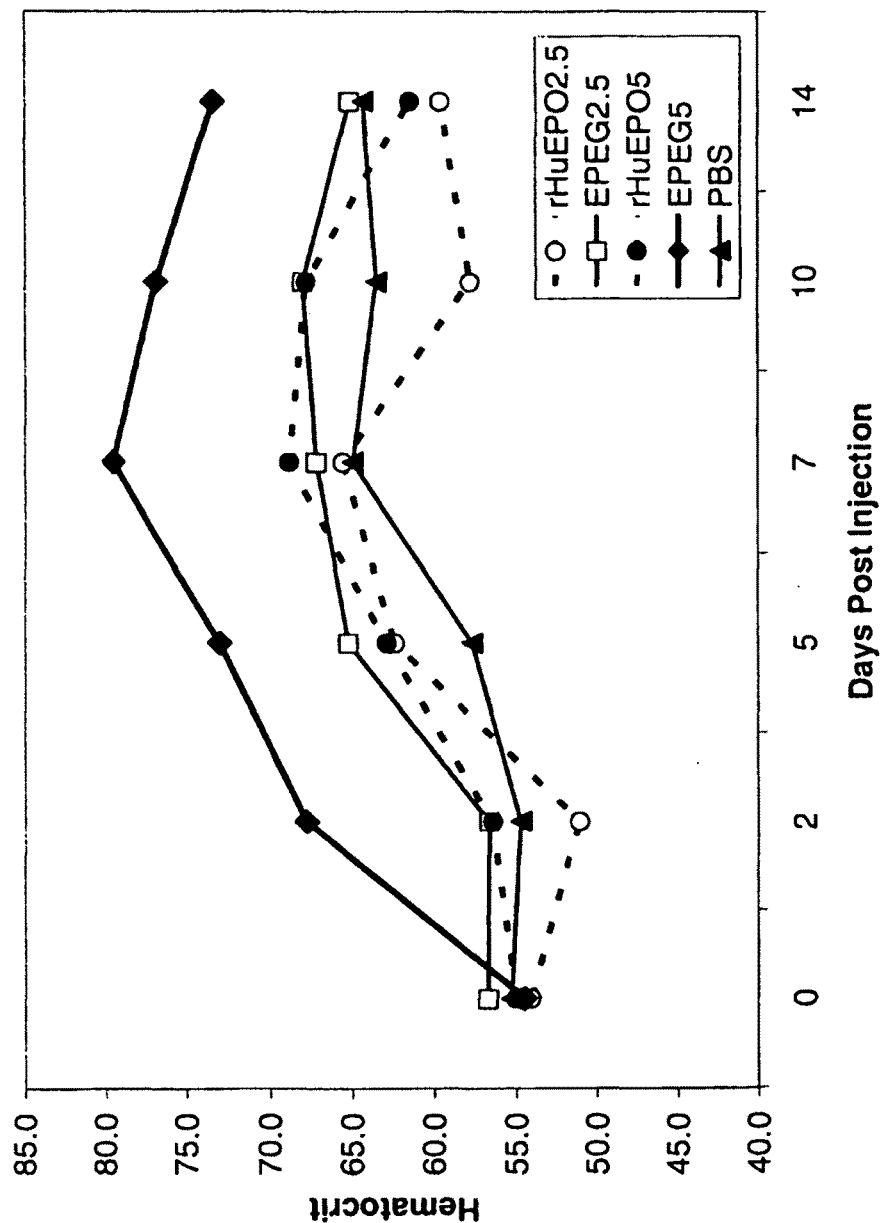

FIG. 10: Time course of hematocrit increase in male Sprague-Dawley rats following bolus injection of EPEG or rhu-EPO (2.5 µg or 5 µg per animal) or vehicle (PBS)

Figure 11:
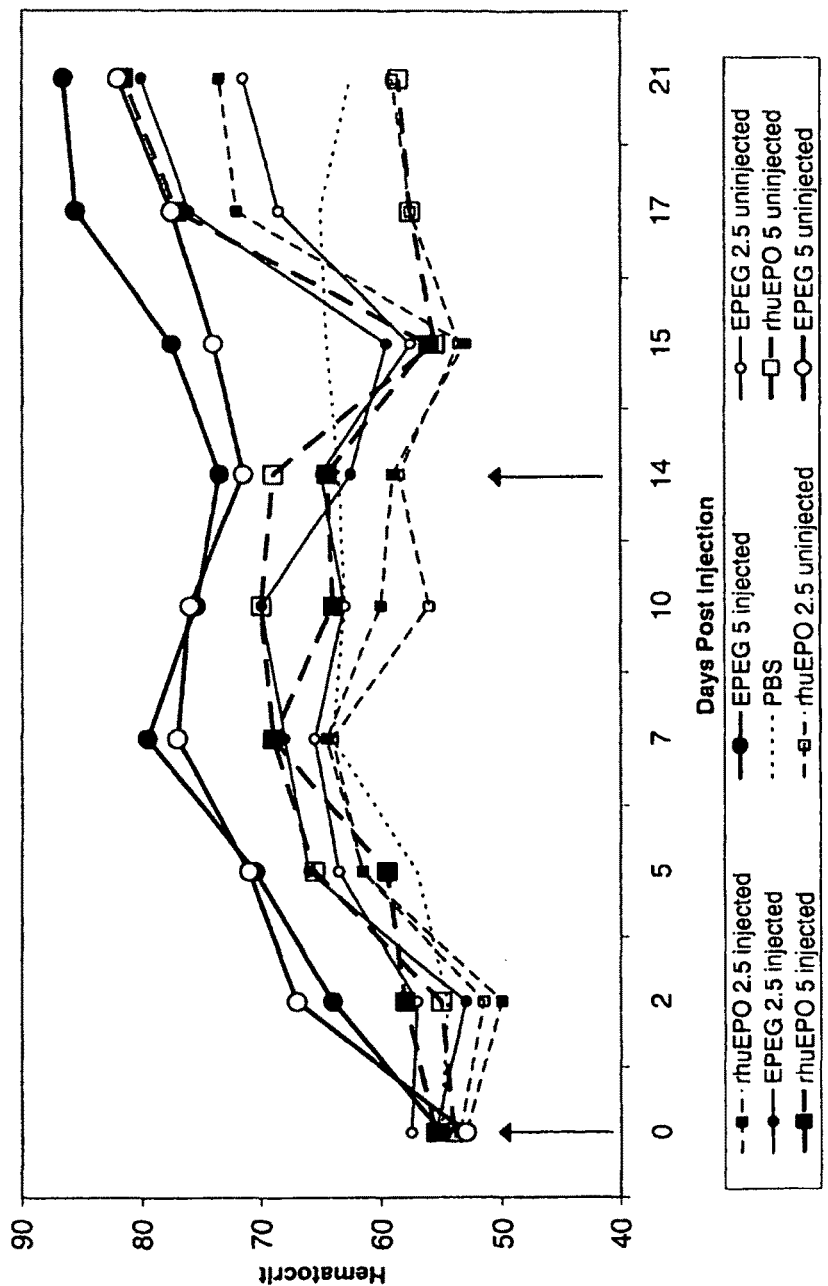

FIG. 11: Time course of hematocrit increase in male Sprague-Dawley rats following one or two ("uninjected" or "injected," respectively) bolus injections of EPEG, rhu-EPO (2.5 µg or 5 µg per animal) or vehicle (PBS). The second administration of EPEG or control occurred 14 days post first administration.

5. DETAILED DESCRIPTION

It is an object of the invention to provide polypeptide conjugates (e.g., EPO-conjugates) that are clinically superior to the non-conjugated polypeptide in its wild type or native form. Moreover, an added benefit of such conjugated polypeptides is that less protein (as compared with the wild type or native polypeptide) can be administered, including on a less frequent basis, to achieve the desired therapeutic effect. This, in turn, results in lower raw material costs and incidence of side effects since the amount of protein per dose is substantially reduced. In certain embodiments, the invention relates to erythropoietin conjugated to water-soluble polymers. In preferred embodiments, the invention relates to polypeptides conjugated to polyethylene glycol (PEG). Most preferably, it relates to erythropoietin conjugated to PEG (EPEG).

In a specific example, compared to native EPO (i.e., EPO without a PEG attached; conventionally glycosylated erythropoietin), the EPO conjugates of the invention, i.e., EPEG, have an increased circulating half-life and plasma residence time, decreased rate of clearance, and increased clinical activity in vivo. The conjugates of this invention have the same uses as EPO. In particular, the conjugates of this invention are useful to increase the red blood cell productions in a subject in need thereof by stimulating the division and differentiation of committed erythroid progenitors in the bone marrow in the same manner that EPO is used to treat the same or similar subjects. Moreover, the inventors have surprisingly found that the conjugates of the invention require no human serum albumin (HSA) in their formulation for stability during storage. As such, the formulations of the invention have the advantage of prolonged stability, lower cost and simplified manufacturing, shipping, storage and quality control relative to currently available EPO-based therapeutics.

As used herein, the term "N-terminus," "amino-terminus," or analogous terms when used in the context of a covalent linkage of a protein to another molecule refer to a covalent linkage via the amino-terminal α-amino group of the protein.

As used herein, the term "wild type" or "native" refers to a protein or polypeptide in its operative or functional form, preferably as it is found naturally functioning in the body. These terms also refer to the protein in a form in which it has not been artificially modified or altered. The terms can thus relate to recombinant proteins. Accordingly, the terms can refer to a protein with an altered glycosylation pattern, including lack of glycosylation, relative to that as produced in the animal from which the nucleic acid and/or amino acid sequence of the protein was originally derived.

As used herein, the "natural function" of a polypeptide means its function prior to covalent modification with a water-soluble polymer. Natural functions include, for example, enzymatic activity, receptor binding (e.g., antibodies), ligand binding, and immunogenicity. Preferably, natural function of erythropoietin refers to the in vivo biological activity of causing bone marrow cells to increase production of reticulocytes and red blood cells.

As used herein, the term "erythropoietin" or "EPO" refers to a glycoprotein, having the amino acid sequence set out in SEQ ID NO: 1 (FIG. 1) or SEQ ID NO: 2 (FIG. 2) or an amino acid sequence substantially homologous thereto, whose biological properties relate to the stimulation of red blood cell production and/or the stimulation of the division and differentiation of committed erythroid progenitors in the bone marrow. As used herein, these terms include such proteins modified deliberately, as for example, by site directed mutagenesis or accidentally through mutations; such that they have additions, deletions, or substitutions of amino acid residues with respect to native EPO. These terms include both natural and recombinantly produced human erythropoietin. EPO refers to both the naturally occurring or recombinant protein, preferably human, as obtained from any conventional source such as tissues, protein synthesis, cell culture with natural or recombinant cells.

Polypeptides substantially homologous to EPO are functional equivalents which include polypeptides with amino acid sequences substantially the same as the amino acid sequence of SEQ ID NO: 1 (FIG. 1) or SEQ ID NO: 2 (FIG. 2). "Substantially the same" in reference to an amino acid sequence is defined herein as a sequence with at least 70%, preferably at least about 80%, and more preferably at least about 90% homology to another amino acid sequence, as determined by the FASTA search method in accordance with Pearson and Lipman, Proc. Natl. Acad. Sci. USA 85, 2444-2448 (1988). Preferably, EPO homologs exhibit equivalent or greater activity as compared to that of native or wild-type EPO as assessed by methods described herein and/or standard methods known in the art.

Any protein having the activity of EPO, such as muteins or otherwise modified proteins, is also encompassed. Recombinant EPO may be prepared via expression in CHO, BHK, COS, HeLa or PER.C6 cell lines or other appropriate cell lines of animal or human origin, by recombinant DNA technology or by endogenous gene activation. Expression of proteins, including EPO, by endogenous gene activation is well known in the art and is disclosed, for example in U.S. Pat. Nos. 5,733,761, 5,641,670, 5,733,746, 5,994,122, 5,733,761, 5,641,670, 5,981,214 and 5,272,071, and international patent publication WO 90/11354 (the contents of each are incorporated herein by reference). Its preparation and therapeutic application are described in detail for example in U.S. Pat. Nos. 5,547,933 and 5,621,080, EP-B 0 148 605, Huang, S. L., Proc. Natl. Acad. Sci. USA (1984) 2708-2712, EP-B 0 205 564, EP-B 0 209 539 and EP-B 0 411 678 as well as Lai, P. H. et al., J. Biol. Chem. 261 (1986) 3116-3121, an Sasaki, H. et al., J. Biol. Chem. 262 (1987) 12059-12076. Erythropoietin for therapeutic uses may be produced by recombinant means (EP-B 0 148 605, EP-B 0 209 539 and Egrie, J. C., Strickland, T. W., Lane, J. et al. (1986) Immunobiol. 72: 213-224), the contents of each of the aforementioned references are incorporated herein by reference. The preferred EPO species for the preparation of erythropoietin glycoprotein products are human EPO species. More preferably, the EPO species is the human EPO having the amino acid sequence set out in SEQ ID NO:1 (FIG. 1) or SEQ ID NO:2 (FIG. 2), and most preferably the amino acid sequence set out in SEQ ID NO:1 (FIG. 1).

Methods for the expression and preparation of erythropoietin in serum free medium are described for example in WO 96/35718, to Burg published Nov. 14, 1996, and in European Patent Publication No. 513 738, to Koch published Jun. 12, 1992 (the contents of each of which are hereby incorporated by reference in their entirety). In addition to the publications mentioned above, it is known that a protein-free fermentation of recombinant CHO cells which contain an EPO gene can be performed. Such methods are described, for example, in EP-A 0 513 738, EP-A 0 267 678 and, in general form, in Kawamoto, T. et al., Analytical Biochem. 130 (1983) 445-453, EP-A 0 248 656, Kowar, J et al., Methods in Enzymology 421 (1986) 277-292, Bavister, B., Expcology 271 (1981) 45-51, EP-A 0 481 791, EP-A 0 307 247, EP-A 0 343 635, WO 96/35718 and WO 88/00967 (the contents of each of which are hereby incorporated by reference in their entirety).

In EP-A 0 267 678 (hereby incorporated by reference in its entirety) an ion exchange chromatography on S-Sepharose, a preparative reverse phase HPLC on a $C_8$ column and a gel filtration chromatography are described for the purification of EPO produced in protein-free culture after dialysis. In this connection, the gel filtration chromatography step can be replaced by ion exchange chromatography on S-Sepharose fast flow. It is also proposed that a dye chromatography on a Blue Trisacryl column be carried out before the ion exchange chromatography.

A process for the purification of recombinant EPO is also described by Nobuo, I. et al., J. Biochem. 107 (1990) 352-359 (hereby incorporated by reference in its entirety). In this process EPO is treated however with a solution of Tween-20, phenylmethylsulfonyl fluoride, ethylmaleimide, pepstatin A, copper sulfate and oxamic acid prior to the purification steps.

As used herein, the term "conjugate" in reference to a protein or polypeptide is a protein or polypeptide or population thereof, that functions in interaction with one or more other chemical groups attached by covalent bonds. Preferably, the protein is erythropoietin or a homolog thereof and the chemical group is a water soluble polymer. Most preferably, the protein is erythropoietin or a homolog thereof and the water-soluble polymer is PEG. The conjugates of the invention have at least one or two PEG molecules linked to each EPO protein. Even more preferably, the conjugates of the invention are made according to the methods disclosed herein.

The pegylated proteins of the invention preferably made according to the methods described herein, are generally referred to as "protein conjugates." In a specific example where the protein is erythropoietin ("EPO"), the molecules of the invention are referred to as "EPO conjugates," "EPEG conjugates," and/or analogous terms, which terms are used interchangeably. These terms "protein conjugate" and/or "protein conjugates" of the invention also refer to a mixture of inventive conjugated proteins, i.e., a plurality of the inventive conjugated protein, e.g., EPO. For example, EPEG conjugate and/or EPO conjugate may refer to a substantially homogenous populations EPO proteins with each EPO protein therein linked with one ("1PEG-EPO;" mono-pegylated EPO) or two ("2PEG-EPO;" di-pegylated EPO) PEG molecules, and or combinations of the foregoing.

Most polypeptides have a plurality of potential PEG linkage sites. Therefore, although a homogenous population of 1PEG-protein conjugates has one PEG molecule linked to each protein molecule, that linkage may not necessarily be in the same location on each protein in the population. Similarly, although a homogenous population of 2PEG-protein conjugates has two PEG molecules linked to each protein molecule, those linkages may not necessarily be in the same locations on each protein in the population. In specific embodiments, the invention encompasses a plurality of EPO conjugates, each conjugate comprising an EPO protein covalently linked to one or two PEG molecules, wherein said plurality comprises an EPO conjugate having at least one of said one or two covalent linkages to PEG molecules(s) via lysine 116. In other embodiments, the invention encompasses a plurality of EPO conjugates, each conjugate comprising an EPO protein covalently linked to one or two PEG molecules, wherein said plurality comprises an EPO conjugate having at least one of said one or two covalent linkages to PEG molecules(s) via the amino terminus of the EPO protein, which covalent linkage at said amino terminus in not through an aldehyde linkage. In still other embodiments, the invention encompasses a plurality of EPO conjugates, each conjugate comprising an EPO protein covalently linked to one or two PEG molecules, wherein said plurality comprises an EPO conjugate having at least one of said one or two covalent linkages to PEG molecules(s) lysine 52, or lysine 154. In other embodiments, the invention encompasses any of the foregoing plurality of EPO conjugates and a conjugate covalently linked to said one or two PEG molecules via any site known in the art to be suitable for such linkage.

In certain embodiments, the plurality of protein conjugates (e.g., the heterogeneous mixture of EPEG conjugates) comprising 1PEG-protein and 2PEG-protein conjugates refers to a mixture of the two aforementioned populations, wherein each population may or may not be homogenous. In specific embodiments, the ratio of the mixture of 1PEG-protein conjugate to 2PEG-protein conjugate is less than about 1 to about 100, about 10 to about 90, about 20 to about 80, about 30 to about 70, about 40 to about 60, about 50 to about 50, about 60 to about 40, about 70 to about 30, about 80 to about 20, about 90 to about 10, or about 100 to less than about 1, wherein less than about 1 includes an amount undetectable using standard methods known in the art.

The "water-soluble polymers" encompassed by instant invention include, but are not limited to, polyalkylene glycol and derivatives thereof, including PEG, methoxylated PEG ("mPEG"), PEG homopolymers, polypropylene glycol homopolymers, copolymers of ethylene glycol with propylene glycol, wherein said homopolymers and copolymers are unsubstituted or substituted at one end with an alkyl group. In preferred embodiments, the polymer is mPEG and most preferably mono-methoxylated PEG. The water soluble polymers can be linear, branched, or star-shaped with a wide range of molecular weights. The size of the PEG can range from 10 to about 100 kD. In specific embodiments, the size of the PEG is about 10 to about 40 kD.

To effect covalent attachment of polyethylene glycol (PEG) and similar poly (alkylene oxides) to a molecule, in particular, a protein, the hydroxyl end groups of the polymer must first be converted into reactive functional groups. This process is referred to herein as "activation" and the product is called "activated PEG," For example, methoxylated PEG ("mPEG") can be activated for subsequent covalent attachment to amino groups by methods well known in the art, i.e., mPEG can be modified to contain varying reactive moieties suitable for subsequent attachment to proteins via amino acid residues containing available amino residues, e.g., lysinyl residues. Such activated mPEG polymers include mPEG-succinimidyl succinate, mPEG-succinimidyl carbonate, mPEG-imidate, and mPEG-cyanuric chloride. For example, methoxy polyethylene glycolyl succinimidyl succinate ("SS-PEG") can be formed from mPEG succinate by reaction with hydroxysuccinimide in the presence of dicyclohexylcarbodiimide (see, e.g., Abuchowski et al. (1984), Cancer Biochem. Biophys. 7:175-186 (hereby incorporated by reference in its entirety)). PEG can be activated by any method known in the art and/or described herein. In certain embodiments, N-hydroxy-succinimidyl-PEG is used as the activated PEG. In preferred embodiments, poly(ethylene glycol)-succinimidyl carbonate ("SC-PEG") is used as the activated PEG (see, e.g., U.S. Pat. No. 5,122,614, which is incorporated by reference in its entirety). In a preferred embodiment, the reaction for covalent attachment of SC-PEG to a protein results in the release of an N-hydroxysuccinidyl group and a PEG-chain attached to the polypeptide through a carbamate linkage via an amino group of the protein (see, e.g., U.S. Pat. No. 5,122, 614). Unlike previous methods known in the art however, and as demonstrated herein using the methods of the invention, the conjugation reaction may be controlled such that the site of pegylation may be preferentially selected (e.g., preferential selection between an amino-terminal α-amino group and an ε-amino group of a lysinyl residue).

In certain embodiments, the invention encompasses methods of activating PEG wherein PEG chloroformate is generated in situ by treatment of the polymer (PEG) with phosgene. The resulting chloroformate is then reacted with N-hydroxysuccinimide (HOSu) followed by triethylamine (TEA) to yield the desired activated derivatives of PEG. The activated polymer preparations may then be purified from the low molecular weight reactants and evaluated for the presence of the theoretical amounts of active groups.

Although any protein may be pegylated according to the methods described herein, the invention, in particular, encompasses the pegylation of therapeutic polypeptides. In certain embodiments, the therapeutic protein for use in accordance with the methods of the invention may be, e.g., a protease, pituitary hormone protease inhibitor, poietin, colony stimulating factor, hormone, clotting factor, anti-clotting factor, neurotropic factor, rheumatoid factor, CD protein, osteoinductive factor, interleukin, growth factor, interferon, cytokine, somatomedian, chemokine, immunoglobulin, gonadotrophin, interleukin, chemotactin, interferon, lipid-binding protein allergen, or a combination of the foregoing. Specific nonlimiting examples of such therapeutic proteins include, interferon-α2A, interferon-α2B, interferon 13, interferon-γ, insulin-like growth factor-1 (IGF-1), insulin-like growth factor-2 (IGF-2), insulin, human growth hormone (hGH), transforming growth factor (TGF), erythropoietin (EPO), ciliary neurite transforming factor (CNTF), thrombopoietin (TPO), brain-derived neurite factor (BDNF), IL-1, insulintropin, 1L-2, glial-derived neurite factor (GDNF), M-1 RA, tissue plasminogen activator (tPA), superoxide dismutase (SOD), urokinase, catalase, streptokinase, fibroblast growth factor (FGF), hemoglobin, neurite growth factor, adenosine deamidase (NGF), granulocyte macrophage colony stimulating factor (GM-CSF), bovine growth hormone (BGH), granulocyte colony stimulating factor (G-CSF), calcitonin, platelet derived growth factor (PDGF), bactericidal/permeability increasing protein (BPI), L-asparaginase, arginase, uricase, γ-interferon, phenylalanine ammonia lyase, follicle stimulating hormone, proinsulin, epidermal growth factor, fibroblast growth factors, nerve growth factor (NGF), tumor necrosis factor, calcitonin, parathyroid hormone (PTH, including human PTH), bone morphogenic protein, hemopoietic growth factors, luteinizing hormone, glucagon, glucagon like peptide-1 (GLP-1), peptide YY (PYY), factor VIIIC, factor IX, tissue factor, and von Willebrand factor, Protein C, atrial natriuretic factor, lung surfactant, bombesin, thrombin, enkephalinase, mullerian-inhibiting agent, relaxin A-chain, relaxin B-chain, prorelaxin, Dnase, inhibin, activin, vascular endothelial growth factor, integrin, protein A or D, bone-derived neurotrophic factor (BDNF), neurotrophin-3, -4, -5, or -6 (NT-3, NT-4, NT-5, or NT-6), CD-3, CD-4, CD-8, CD-19, M-CSF, GM-CSF, G-CSF, biologically active fragments of any of the foregoing, or combinations of the foregoing. In preferred embodiments, the protein or polypeptide is native EPO.

The preferred conjugates are made by reacting native protein or polypeptide with an activated water-soluble polymer. Preferably, the water-soluble polymer is PEG. Even more preferably, the water-soluble PEG is mPEG. Preferably, the mPEG has a molecular weight of about 10 to about 100 kD, more preferably, about 10 kD to about 50 kD, even more preferably about 10 kD to about 25 kD and most preferably, about 12 kD. In certain embodiments, the activated PEG is N-hydroxy-succinymide-PEG ("NHS-PEG"). In preferred embodiments, the activated PEG is a succinimidyl carbonate ester ("SC-PEG"). Preferably, the activated PEG and the native EPO react in a reaction buffer.

Variant EPEG (i.e., EPO conjugate) formulations were produced using multiple species of activated PEG. All formulations tested, excepting that manufactured using 40 kD branched-PEG, demonstrated higher activity than native EPO in an in vivo rat model of hematocrit induction. This result was independent of whether SC-PEG or NHS-PEG was used or whether the molecular weight of the PEG was 12 kD or 20 kD, or whether the shape of PEG was linear or branched.

The "reaction buffer" as used herein is a standard buffer free of amine components, e.g., phosphate buffered saline (PBS). Preferably, the reaction buffer has a salt, e.g., Na, concentration of about 0.1 mM to about 100 mM, most preferably about 1 mM to about 50 mM, and even more preferably about 10 mM to about 20 mM. In certain embodiments, the polypeptide is mixed with the dry activated water-soluble polymer under stirring. Preferably, the reaction buffer has a pH of about 6.5 to about 8.5 or about 6.6 to about 7.5. In preferred embodiments, the reaction buffer has a neutral pH of about 7.0. In certain embodiments, the molar ratio of protein (e.g., EPO) to activated water-soluble polymer in the reaction buffer is about 1 to about 3 to about 1 to about 60. In other embodiments, the reaction buffer comprises a molar ratio of protein (e.g.) to activated water-soluble polymer of about 1 to about 6, to about 1 to about 60. In preferred embodiments, the reaction buffer comprises a molar ratio of erythropoietin protein to activated water-soluble polymer of about 1 to about 7. The preferred reaction condition is a neutral reaction buffer of about pH 7.0 and comprising a molar ratio of water-soluble polymer to polypeptide of about 7 to about 1.

In certain other embodiments, the reaction buffer may further comprise an organic solvent. In such embodiments, the preferred organic solvent is dimethyl sulfoxide ("DMSO"). The DMSO may be present in the reaction mixture in concentration of 5-80% and, preferably 10-40% (v/v). DMSO is widely used as a general solvent, but not for affecting pegylation reactions, in particular, for preferentially affecting the resulting sites of pegylation of said reaction. The reaction conditions described herein appear to specifically drive the covalent conjugation of the activated PEG toward particular lysine sites. Moreover it has now been found that addition of DMSO to the reaction buffer alters the sites of pegylation. In particular, the addition of DMSO to the reaction buffer as described herein drives the reaction toward the preferential pegylation of the protein at its amino-terminus, i.e., the amino-terminal α-amino group. Accordingly, the methods of the invention allow for selective modification of specific amino groups of the protein of interest, in particular, modification of the amino terminus of the protein. This selective modification of such proteins is beneficial in that it has been generally understood that associating water-soluble polymers, e.g., PEG, with proteins via amino-groups resulted in a loss of activity. It is believed that loss of activity commonly associated with pegylation was due to the random, lysine-targeted reactions of the prior art. Random modification of lysine residues may inadvertently alter protein function by substantially altering the tertiary structure or morphology of said protein. While not wishing to be limited to any theory in any way, the reaction conditions disclosed herein appear to enable the selective modification of a protein at select residues or at its amino terminus, which is not generally believed to contribute to the activity of a protein. In a specific example, the methods of the invention are used to link one to two PEG molecules to specifically those EPO lysine residues whose linkage to PEG does not result in a loss of biological activity relative to native EPO but rather results in EPO conjugates that are surprisingly more clinically effective than native EPO.

Amino-terminal specific pegylation of proteins has previously been reported using aldehyde activated PEG. However, such reaction were only specific at low pH, losing specificity at a pH of 7 or higher (see, e.g., U.S. Pat. Nos. 6,077,939 and 5,985,265, each of which is hereby incorporated by reference in its entirety). Accordingly, the methods of the instant invention may be of particular use in the pegylation and/or conjugation of pH sensitive proteins.

In the preferred reactions, the activated water-soluble polymer will be present in molar excess and as such, the unreacted excess activated water-soluble polymer will need to be removed from newly formed protein conjugates. As used herein, "removing substantially all unlinked water-soluble polymer" refers to generally known methods for carrying out such a separation, e.g., through dialysis. Generally, about 80% of unlinked water-soluble polymer is removed, preferably about 90% is removed, more preferably about 95% is removed and most preferably about 99% is removed.

The invention provides protein conjugates, in particular, EPO conjugates, said conjugates comprising an erythropoietin glycoprotein having at least one water-soluble polymer attached thereto and having the in vivo biological activity of causing bone marrow cells to increase production of reticulocytes and red blood cells. In preferred embodiments, the EPO glycoprotein is a human erythropoietin and/or analogs thereof having the sequence of human erythropoietin (e.g., SEQ ID NO:1 (FIG. 1); SEQ ID NO:2 (FIG. 2)) or an amino acid sequence substantially identical thereto.

The specific activity of EPO or EPEG conjugates can be determined by methods described herein or standard assays known in the art. The biological activity of the purified EPO conjugates of the invention are such that administration of the inventive formulations (e.g., a plurality of EPO conjugates of the invention, or one or more components thereof, and a pharmaceutically acceptable carrier) to human patients results in bone marrow cells increasing production of reticulocytes and red blood cells relative to that of non-injected or control groups of subjects. The biological activity of the EPO conjugates, or fragments thereof, obtained and purified in accordance with the methods of the invention can be tested by methods, e.g., according to Annable, et al., Bull. Wld. Hlth. Org. (1972) 47: 99-112 and Pharm. Europa Spec. Issue Erythropoietin BRP Bio 1997 (2).

As used herein, "capable of reaching a serum level at least about 25%, 30%, 35%, 40%, 45% or 50% higher than native erythropoietin about 36 hours after injection into Sprague-Dawley rats," refers to the fact that the EPEG conjugates of the invention are cleared from the subject in an in vivo assay using Sprague-Dawley rats, at a substantially slower rate than native EPO or commercially available glycosylated EPO resulting in a higher and broader PK profile relative to that of control compounds. Serum levels of the inventive EPEG conjugates can be readily determined by those of skill using routine methods in the art, for example, but not limited to, radiolabeling and immunoassay. Preferably, serum levels are determined according to the methodology described in Example 4 infra.

Example 4 demonstrates that native EPO reaches its greatest serum concentration (i.e., achieves the highest blood borne activity of radiolabeled EPO conjugate) soon after it is injected and is then eliminated within 13 hours. A currently available glycosylated-EPO therapeutic, ARANESP® (darbopoietin alfa) (Amgen, Thousand Oaks, Calif.), has a peak blood-borne radioactivity at 12-18 hours after injection and exhibits a longer half-life than native EPO. However, ARANESP® (darbopoietin alfa) fails to reach significantly higher concentrations in the blood than native EPO. In contrast, the concentration of blood-borne activity of EPEG conjugates of the invention are similar to both EPO and ARANESP® (darbopoietin alfa) over the initial about 12 hours; however, following about 12 hours, the concentration of activity of EPEG conjugates in the serum continued to increase and reached a maximal level about 50% higher than either EPO or ARANESP® (darbopoietin alfa) at 36 hours post injection. EPEG is cleared from the body about 26% to about 38% slower than ARANESP® (darbopoietin alfa). As a result, EPEG conjugates provide an increased total drug exposure, in terms of the area under the curve, than either the control EPO or ARANESP® (darbopoietin alfa). In fact, EPEG has an about 25% to an about 45% greater area under the curve (AUC) than ARANESP® (darbopoietin alfa); and 4 times greater AUC than native-EPO (see Example 4). As a result, EPEG may be administered less frequently than native EPO or other glycosylated-erythropoietin formulations, for example, ARANESP® (darbopoietin alfa), while still achieving higher levels of biological activity.

The working examples provided herein further demonstrate that the conjugates of this invention can be used in the same manner as unmodified polypeptides. Specifically, the EPEG conjugates disclosed herein may be used in the same manner as native EPO. However, the conjugates of the invention have at least two unexpected, superior properties relative to prior pegylated polypeptides known in the art. Specifically, the EPEG conjugates of the invention have unexpectedly high potency relative to control formulations and can be stored for prolonged periods of time in a protein free formulation (i.e., stored in a protein-free pharmaceutically acceptable carrier). The experimental results disclosed herein demonstrate that the conjugates of this invention have an increased circulating half-life and plasma residence time, decreased clearance rates and increased clinical activity in vivo relative to control formulations.

While not wishing to be bound or limited to any specific theory in any way, it is theorized that the increased in vivo activity of the EPEG formulations of the invention relative to control formulations may be due to the increased plasma half-life. On receptor binding, native EPO and its receptor are known to be processed and internalized by the cell. Once all EPO receptors are bound and internalized, EPO signaling has been maximized and cells are rendered insensitive to any excess native EPO still present in the body. As is demonstrated in the working examples herein, excess native EPO is then rapidly excreted by the body. It is believed that the increased biological activity of plurality of EPO conjugates of the invention, or one or more components thereof, may then be a function of the increased bioavailability and the increased half-life (i.e., increased circulation time) as compared to the receptor turnover time. Once an EPO-receptor is internalized, it requires a period of time for a new receptor to take its place. The circulating life of plurality of EPO conjugates of the invention, or one or more components thereof, may be sufficiently long to bind to multiple generations of receptors prior to elimination. The EPO conjugates of the invention thereby increase in vivo activity lycosylated EPO formulations.

Because of these improved properties, the conjugates of this invention may be administered at reduced dosages and/or reduced schedules relative to those of unmodified EPO or currently available EPO-based, e.g., increase hematocrit induction, relative to that of native EPO or currently available g formulations, e.g., once weekly instead of the three times weekly, respectively. The EPO conjugates of the invention may also be given to a subject in need thereof at least once daily, at least once every other day or at least once every third day. It is preferable, however, that an EPO conjugate formulation of the invention may be given to a patient in need thereof, at least once a week. More preferably, an EP) conjugate formulation of the invention may be given to a patient at least once every two weeks. Most preferably, the an EPO conjugate formulation of the invention may be given to a patient at least once a month or at least once every 6 weeks to two months.

Decreased frequency of administration is expected to result in improved patient compliance leading to improved treatment outcomes, as well as improved patient quality of life. Compared to conventional glycosylated-EPO, it has been found that conjugates having the molecular weight and linker structure of the conjugates of the invention have an improved potency, stability, circulation AUC, circulating half-life, and cost of goods profile.

5.1 Prophylactic and Therapeutic Methods

The protein conjugates of the invention may be used as the native protein is used. For example, EPEG formulations may be used as EPO is used, e.g., in treatment of anemia due to kidney diseases, cancer complications, chemotherapy, or HIV therapies. Other specific potential applications in accordance with this aspect of the invention include all diseases for which expansion of red blood cell would be beneficial to the patients (e.g., anemia). The exact amount of conjugate is a matter of preference subject to such factors as the exact type of condition being treated, the condition of the patient being treated, as well as other ingredients in the composition.

The therapeutically effective amount is that amount of conjugate necessary for the in vivo biological activity of causing bone marrow cells to increase production of reticulocytes and red blood cells. The exact amount of conjugate is a matter of preference subject to such factors as the exact type of condition being treated, the condition of the patient being treated, as well as the other ingredients in the composition. The pharmaceutical compositions containing the conjugate may be formulated at a strength effective for administration by various means to a human patient experiencing blood disorders characterized by low or defective red blood cell production. Average therapeutically effective amounts of the conjugate may vary and in particular should be based upon the recommendations and prescription of a qualified physician. For example, 0.01 to 10 µg per kg body weight, preferably 0.1 to 3 µg per kg body weight, may be administered e.g. once weekly. Alternatively, the pharmaceutical compositions of the invention may contain different amounts of EPEG, e.g. from about 10 to about 1000 µg/ml, preferably from about 50 µg/ml to about 400 µg/ml.

However, the skilled artisan will recognize that the pharmaceutical compositions containing the conjugates of the invention may be formulated at a strength effective for administration by various means to a human patient experiencing blood disorders characterized by low or defective red blood cell production. Average therapeutically effective amounts of the conjugate may vary and should be based upon the recommendations and prescription of a qualified physician.

5.1.1 Pharmaceutical Compositions

The compositions of the invention, e.g., the plurality of protein or erythropoietin glycoprotein conjugates, or one or more components thereof, prepared in accordance with this invention may be further rendered suitable for injection by mixture or combination with an additional pharmaceutically acceptable carrier or vehicle by methods known in the art. Among the pharmaceutically acceptable carriers for formulating the products of the invention are saline, human serum album, human plasma proteins, etc. The invention also relates to pharmaceutical compositions comprising a conjugate as described above and a pharmaceutically acceptable excipient and/or carrier. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The protein conjugates prepared in accordance with this invention may be formulated in pharmaceutical compositions suitable for injection with a pharmaceutically acceptable carrier or vehicle by methods known in the art. See, e.g., WO97/09996, WO97/40850, WO98/58660, and WO99/07401 (each of which is hereby incorporated by reference in its entirety). The compounds of the present invention may be formulated, for example, in 10 mM sodium/potassium phosphate buffer at pH 7 containing a tonicity agent, e.g. 132 mM sodium chloride. Optionally, the pharmaceutical composition may contain a preservative.

Preferably, the pharmaceutical compositions comprise an EPO conjugate as defined above, a multiply charged inorganic anion in a pharmaceutically acceptable buffer suitable to keep the solution pH in the range of from about 5.5 to about 7.0, and optionally one or more pharmaceutically acceptable carriers and/or excipients. For example, the composition of the invention may comprise from about 10 µg to about 1000 µg erythropoietin conjugate per ml, 10-200 mmol/l sulfate, about 10 to about 50 mmol/l phosphate pH 6.0 to 6.5, optionally up to about 1 mM $CaCl_2$, and optionally about 1-5% of a polyol.

The EPEG conjugates of the invention have been shown to be resistant to degradation or loss of EPEG activity after at least 15 months of storage at low temperature (e.g., −20° C., 4° C.) or at least 10 months of storage at elevated temperature (e.g., 25° C., 37° C.) in protein-free solution and are expected to retain such stability for an extended period of time. The EPEG conjugates of the invention in such protein-free formulations may also be stable enough to ship and store under normal conditions, such as at room temperature. In comparison, commercially available EPO, e.g., EPREX® (epoetin alfa), requires 0.2% human serum albumin (HSA) for protection and is shipped and stored at reduced temperature. Pharmaceutical formulations containing human biological or serum derived ingredients such as HSA are subject to more stringent manufacturing requirements and regulatory compliance; and, as a result, are associated with substantially greater costs. It is possible, however, to formulate the inventive protein conjugates, e.g., EPO-conjugates, in a protein-free salt buffer without loss of the active pharmaceutical ingredient. As such, the ability to deliver a drug (e.g., EPEG) in a protein-free pharmaceutically acceptable carrier is of major economic advantage.

Therefore, in the most preferred embodiment, the pharmaceutical composition is made up of EPEG conjugate and a protein-free pharmaceutically acceptable carrier. Optionally, the protein-free pharmaceutically acceptable carrier may include non-protein excipients to further enhance the pharmacological properties of the EPEG conjugates. These include but are not limited to sugars such as mannitol, amino acids such as histidine, or a low level of conventional surfactants such as tween-80, etc.

The invention will be better understood by reference to the following examples which illustrate but do not limit the invention described herein

6. EXAMPLES

6.1 Example 1

Pegylation of EPO by SC-PEG-12K

Mono-methoxylated PEG (molecular weight 12,000 KD) activated as a succinimidyl carbonate ester (SC-PEG-12K) was used as the pegylating reagent. EPO produced in CHO cells was used as the polypeptide. The EPO-protein (50 mg) was prepared at a concentration of 0.61 mg/ml in a reaction buffer containing 0.15 mM NaCl, and 10 mM sodium phosphate, at pH 6.9. For certain experiments, the reaction buffer also contained 15% DMSO.

The polypeptide solution was mixed with the dry PEG reagent while stirring to reach the final PEG/EPO molar ratio of 7:1. The products of the reaction, including DMSO, and un-reacted PEG molecules were separated by dialysis using a membrane having a molecular weight cut off of 25,000 KD. Regardless of the reaction buffer composition, i.e., with or without DMSO, the final product contained a mixture of mono-pegylated EPO and di-pegylated EPO of approximate equal proportion, as determined by polyacrylamide gel electrophoresis (PAGE) (see, e.g., FIG. 3B). The product prepared in this fashion was designated as EPEG.

6.2 Example 2

Sites of Pegylation

SC-PEG (12 kD) was used to pegylate EPO according to the protocol of Example 1, and the resulting EPEG formulations or EPO (control) were subjected to tryptic digestion as standard in the art: 100 pico-moles of the protein was digested with TPCK-treated trypsin (Sigma, Mo.), at 4% of the weight of the substrate in 100 mM sodium phosphate pH8.4 at 37.0 for 18 hours. The digest was analyzed on C18 reverse phase column (Apollo C-18, 5 u particle, 4.6×100 mm). The fragments were eluted using a linear gradient of 50 minutes from 100% of 0.125% TFA (trifluoroacetic acid) to 75% of acetonitrile/0.125% TFA. Eluted fragments were analyzed by UV wavelength at 230 nm. Example chromatograms are shown in FIGS. 3A and 3B for EPO and PEG-EPO, respectively. Peaks that were present in the EPO chromatogram but diminished or absent in the PEG-EPO elution profile indicate PEG modification and were characterized for their pegylation sites.

The fractions that contained PEG were analyzed by protein sequencing according to standard procedure using the ABI Procise system. (ABI, CA). Pegylation sites were determined by matching the detected sequence with the amino sequence of EPO. Results are presented in Table 1.

TABLE 1

Sites of Pegylation from multiple PEG-EPO Lots Prepared According to Example 1, With and Without DMSO in the Reaction Mixture

| Lot number of PEG-EPO | Pegylation Sites (as % of total modified sites) | | | | Presence of DMSO |
|---|---|---|---|---|---|
| | N-terminus | lysine-52 | lysine-116 | lysine-154 | |
| 5d29-ty | 20 | 36.4 | 36.4 | 7.2 | no |
| 5012V | 41 | 36 | 23 | | no |
| 501P-c | 16 | 54 | 30 | | no |
| x6012 | 22 | 68 | 5 | 5 | no |
| L33 | 14 | 86 | | | no |
| 7517A | 92 | 8 | | | yes |
| 68291 | 87 | 13 | | | yes |
| 6213V | 81 | 19 | | | yes |
| 6214Ty | 79 | 7.5 | 10 | 3.5 | yes |

Surprisingly, it was found that the presence of DMSO in the reaction buffer shifted the pegylation reaction to preferentially, and predominantly, pegylate the N-terminus (i.e., the α-amino group) of the protein. In particular, the presence of DMSO shifted the reaction from the pegylation of lysine 116. Previous reports had demonstrated pegylation of the N-terminus of proteins using only aldehyde-activated PEG and acidic pH (see, e.g., U.S. Pat. Nos. 6,077,939 and 5,985,265, each of which is hereby incorporated by reference in its entirety).

The preferential pegylation enabled by the addition of DMSO to the reaction buffer was confirmed using N-terminal sequencing. Undigested EPO or its counterpart EPEG prepared according to example 1 (with DMSO) were subject to N-terminal sequencing according to standard methods. When compared more than 50% of the expected amount of the N terminal alanine could not be detected in the EPEG sample, confirming the above results. Similar results were also achieved with proteolytic protection analysis using proteases such as stapholoccus ProteaseV8, chymotrpsin, or trypsin.

Preliminary data also indicate that the pegylation methods of the invention also enable the selective pegylation of other proteins, including the selective pegylation of the N-terminus of the protein. For example, when the protein granulocyte-colony stimulating factor (G-CSF) was pegylated according to the methods of Example 1, using SC-PEG and DMSO, and subsequently purified on an SP column, the PEG-GCSF eluted at the same time, i.e., in the same fraction, as that of the N-terminal modified species of the invention; in the absence of DMSO, the elution time was shifted. The results suggest that the methods of the invention likely enable the selective pegylation of proteins and, in particular, the targeted pegylation of the α-amino group.

6.3 Example 3

Formulation and Stability of PEG-EPO

EPEG was prepared according to the methods of Example 1, using reaction buffer containing DMSO. The product was filtered through a 0.2 μM membrane to reduce the bioburden, and was then diluted with PBS (phosphate buffered saline pH 6.9) to a final concentration of 50 μg/ml as determined by a BCA protein assay described infra. The product was sterile filtered into 1 ml vials for storage. The finished product was tested by the LAL test (*Limulus Amebocyte* Lysate pyrogen assay, Cambrex, Md.) and had an endotoxin level of less than 0.1 EU per ml. These vials were stored at 37° C., 25° C., 4° C. or −20° C. for subsequent stability and/or activity testing. Periodically, samples were tested for physical integrity by PAGE, for protein content by BCA protein assay, and for EPO activity by stimulation of the growth of the stem cells and hematocrit production. (See Example 3 for activity assays).

There was no evidence of degradation or loss of EPEG after 15 months of storage at −20° C. or 4° C. by SDS PAGE (see, e.g., FIG. 5, lanes 2 and 3, respectively). Surprisingly, SDS PAGE also indicated no detectable loss of physical integrity after storage for at least 10 months at either 25° C. or 37° C. (FIG. 5, lanes, 4 and 5, respectively), even though there were no carrier proteins such as HSA (human serum albumin) present as an excipient to protect the drug. In comparison, the commercial EPO, EPREX® (epoetin alfa), requires 0.2% HSA for protection. It is, therefore, possible to formulate the inventive protein conjugates in a protein free salt buffer without loss of the active pharmaceutical ingredient, EPEG. The stability of the sample was also evaluated by the BCA protein content assay.

The stability of the sample was also evaluated by BCA protein content assay. Representative samples stored at 37° C., 25° C., 4° C. or −20° C. were selected for a BCA protein assay (Pierce Chemical Co, MN) to quantify the total protein concentrations. 50 ul of sample or control was incubated in 175 ul of working reagent solution for 2 hours at 37° C. and the absorbance at 650 nm determined. A 4-parameter regression was performed to determine the protein concentrations. A standard curve was generated with BSA (bovine serum albumin) and had a correlation coefficient of 0.999. After 12 weeks of storage, the assay determined a protein concentrations of 50.5 µg/ml for the samples stored at 37° C., and 51.3 µg/ml for the samples stored at 25° C. After 47 weeks of storage, the assay determined protein concentrations of 51.4 µg/ml for the sample stored at −20° C. and 49.5 µg/ml for the sample stored at 4° C. At start of the experiment, the samples had concentrations of approximately 50 µg/ml determined by BCA. Therefore, there was no loss of protein over time. Note that EPREX® (epoetin alfa) cannot be used as standard in the BCA assay because it contains 0.2% HSA.

Further evidence of the stability of the samples was observed when the samples were evaluated for their potency to induce stem cell differentiation (as described in Example 4) in an accelerated study. The activity was evaluated at 3 units/ml product and is expressed as percentage of colony formation induced by the same dose of EPREX® (epoetin alfa). The samples stored at 37° C. for 12 weeks had 76.3% of control activity, those stored at 25° C. for 17 weeks had 76.5%, those stored at 4° C. for 54 weeks had 85.3%, and those stored at −20° C. for 47 weeks had 77.9%. The sample at time 0 had 76.5% of control activity; indicating that approximately 100% of the original activity was preserved during storage in carrier-protein free formulations.

6.4 Example 4

Evaluation of the Functional Effects of PEG-EPO on Erythroid Progenitor Proliferation Using Methylcellulose-Based In Vitro Colony Assays EPEG was prepared according to the methods of Example 1, using a reaction buffer without DMSO. The potency of EPEG was evaluated by the ability to stimulate stem cell differentiation into erythroid cells. Normal human bone marrow was used as the source of stem cells. The light density cells were obtained after Ficoll separation, (kit from Poietics Inc). The cells were resuspended in 10 ml of Iscove media containing 2% FBS and checked for viability with trypan blue. EPEG test samples at (50 µg/ml) and control samples were converted into units/ml for comparison assuming the standard 125,000 units/mg of EPO subsequent to the determination of protein concentration by BCA protein assay as described in Section 6.2. For the colony forming cells (CFC) assay, a stock solution of 300 units/mL was made and serial dilutions were prepared in Iscove media containing 2% FBS.

As a control, a similar stock solution of EPREX® (epoetin alfa) (20,000 IU/ml, lot#58B097) was also prepared for plating. Standard EPO (EPREX® (epoetin alfa)) and EPEG were added to a final concentration of 3, 1, 0.3, 0.1 and 0.03 units/ml. Hematopoictic colony assays were initiated with 20,000 bone marrow cells per culture. All cultures were setup in triplicate and incubated for 14 days. On day 14, colony numbers were scored. The colonies were divided into the following categories, based on morphology, CFU-E, BFU-E and CFU-GM as is routine in the art. CFU-E is an erythroid colony derived from a more mature progenitor and contains less than 200 erythroblasts. BFU-E is an erythroid colony derived from a primitive cell and contains greater than 200 erythroblasts. CFU-GM is the colony derived from a colony forming cell (CFC) capable of producing colonies with 40 or more granulocyte and/or macrophage cells. The total erythroid (CFU-E+BFU-E) as well as the total CFC (total erythroid+CFU-GM) were quantified. Assay using media only generated no detectable erythroid colonies. This validates that the observed the colonies are due to the test samples. The result shows that in the progenitor assay a dose dependent effect on erythroid progenitor growth for both the control EPREX® (epoetin alfa) and test EPEG, in the absence of added cytokines. At saturating concentrations of 3 u/ml, EPEG A, B, and C induce 78-82% of EPREX® (epoetin alfa) control growth. The levels are lower at sub-saturation concentrations (1 and 3 units/mL), as shown in FIG. 6. The graph shows the average number of 3 readings. The average coefficient of variation is 11% for 3 unit/ml, 25% for 1 unit/ml, 30% for 0.3 units/ml, and 50% for 0.1 unit/ml. The p-values for the confidence levels were P<0.01. After five months of storage in a protein free media, EPEG samples maintained full activity. Assay results were subjected to statistical analysis. Standard t-tests were performed to assess the difference in the number of colonies generated between cultures tested with EPO and the PEG-EPO at equivalent concentrations. A p value of less than 0.01 is deemed significant. The observed data indicate the result is within this significance level. Similar results were obtained using EPEG prepared in reaction buffer containing DMSO.

6.5 Example 5

Pharmacokinetics Study of EPEG (PEG-EPO)

Two different lots of EPEG (EPO-PEG201 and EPO-PEG202) were prepared according to the methodology of Example 1 using reaction buffer without DMSO (i.e., native EPO was modified by SC-PEG-12K at the lysine sites) and the resulting protein concentrations of the samples determined by BCA assay as described in section 6.3. These EPEG compounds were used to compare the pharmacokinetic profile to the native, unmodified, naturally functional EPO and the FDA-approved EPO-hyperglycosylated (ARANESP® (darbopoietin alfa), from Amgen, Inc., Thousand Oaks, Calif.). ARANESP® (darbopoietin alfa) was used as a benchmark because it is an FDA-approved product and has a prolonged half life due to hyperglycosylation of the protein. To detect the proteins in the blood, the four samples (EPO-native, EPO-PEG201, EPO-PEG202 and ARANESP® (darbopoietin alfa)) were labeled with $^{125}$I at their tyrosine sites using the Chloramine T method as known in the art. Each molecule had about 1-2 $^{125}$I attached. Each sample (80 µg) was labeled and separated from residual unbound $^{125}$I using a desalting column. The activity of the proteins was detected and verified on a polyacrylamide gel and a reverse phase column. The pegylated samples were evaluated for the subpopulation of EPO that is conjugated to one PEG molecule (1PEG-EPO), or the subpopulation of EPO that is conjugated to 2 PEG molecules (2PEG-EPO). 1PEG-EPO to 2PEG-EPO ratios were 54:46 in EPO-PEG201; and 45:55 in EPO-PEG202. To analyze the pharmacokinetic profile of the four radio-labeled protein batches, protein solutions at the dosage of 4 Ci/kg body weight were injected subcutaneously into male Sprague-Dawley rats. The rats were divided into 5 subgroups with 4 animals each to avoid more than 3 blood samplings for each animal. Blood samples were taken at different time points after injection (0, 0.5, 1, 2, 4, 8, 12, 16, 24, 36, 48, 72, 96 and 120 hours). The amount of radio-labeled protein in the blood sample was determined using a scintillation counter and the generated data were statistically evaluated. Results are shown in FIG. 7. EPO-PEG201 and EPO-PEG202 have similar pharmacokinetic profiles. Surprisingly, the Inventors discovered that both have a higher and broader PK profile than either ARANESP® (darbopoietin alfa) or native EPO. Table 2 shows the results of the analysis of the PK parameters using a one-compartment model and dosage accumulation.

TABLE 2

Pharmacokinetic parameters of four EPREX ® (epoetin alfa) and EPO-PEG

|  | Tmax(hr) | Cmax(pCi/ml) | AUC(pCi*h/ml) | half-life |
|---|---|---|---|---|
| EPO | 8.84 | 3208 | 96240 | 12.84 |
| EPO-PEG201 | 21.69 | 4139 | 333400 | 32.53 |
| EPO-PEG202 | 20.02 | 5199 | 386600 | 30.03 |
| ARANESP ® | 15.8 | 4072 | 267300 | 23.64 |

Native EPO reached a high level as soon as it was injected and was eliminated within 13 hours. ARANESP® (darbopoietin alfa), the currently approved long-acting form of EPO, peaked at 12-18 hours and exhibited a longer half-life than EPO but failed to reach significantly higher concentrations in the blood. The blood levels of EPEG made according to the methods disclosed herein, were similar to both EPO and ARANESP® (darbopoietin alfa) for the initial 12 hours, after which time the activity concentration continued to increase and reached a maximal level about 50% higher than either EPO or ARANESP® (darbopoietin alfa) at 36 hours. EPEG was cleared from the body about 26% to about 38% slower than ARANESP® (darbopoietin alfa). This results in a superior total exposure, in terms of the area under the curve, than either the control EPO or ARANESP® (darbopoietin alfa). In fact, EPEG has an about 25% to an about 45% greater area under the curve (AUC) than ARANESP® (darbopoietin alfa); and 4 times greater than native-EPO.

6.6 Example 6

Production of Various Forms of PEG-EPO

Multiple batches of EPEG were prepared according to the methods of Example 1, using reaction buffer without DMSO and using different varieties of activated PEG. The amount of activated PEG used in the pegylation reaction was adjusted such that the final product contained approximately equal amounts of 1PEG-EPO and 2PEG-EPO. 1PEG-EPO and 2PEG-EPO were purified using DEAE column chromatography. The column was equilibrated with a buffer containing 75 mM NaCL, 5 mM sodium phosphate at pH 6.75. After reaction, the sample was dialyzed against the same buffer, and then loaded onto the column for purification. Small amounts of highly modified PEG-EPO did not bind to the column and eluted in the wash. The samples were eluted with a gradient to 97.5 mM NaCL, 5 mM sodium phosphate pH 6.75. Any native EPO was eluted with 150 mM NaCL in sodium phosphate buffer pH 6.75. Eluted fractions were evaluated by polyacrylamide gel electrophoresis. The fractions were separated into 3 groups: 1PEG-EPO, 2-PEG-PEG and an equal mixture of the two. Five representative samples were produced: Y501P, EPO modified by branched chain NHS-PEG (20 kD) with 1PEG-EPO; Y502P, EPO modified with branched chain NHS-PEG (20 kD) with 2PEG-EPO; Y5012, EPO modified by branched chain NHS-PEG (20 kD) with equal amount of 1PEG-EPO and 2PEG-EPO; L33, EPO modified with linear chain SC-PEG (12 kD) with equal amount of 1PEG-EPO and 2PEG-EPO; and X6012, EPO modified with branched NHS-PEG (40 kD) with equal amount of 1PEG-EPO and 2PEG-EPO. Protein concentrations of the final samples were determined as described in section 6.3.

6.7 Example 7

Pharmacodynamic Studies of PEG-EPO Variants

EPEG samples produced as outlined in Example 6 were administered to rats to compare and evaluate activity: Y501P (1PEG-EPO), Y502P (2PEG-EPO) and Y5012 (mix 1 PEG-EPO and 2PEG-EPO).

Sprague-Dawley rats (specific pathogen free, 5 weeks old, male) were housed in filter-top cages in an air-conditioned animal facility. Water was provided ad libitum. Rats are adapted for one week after arrival before the study. EPEG samples were diluted with PBS before injection. The rats (each approximately 250 g) were injected subcutaneously with 5 μg total protein in 1 ml of buffer (PBS) or 1 ml PBS (control) and hematocrit was monitored over 25 days. Hematocrit was determined by drawing blood from the tail vein into a heparinized capillary tube (Marienfld, Germany). After sealing, the capillary tubes were centrifuged with a hematocrit centrifuge (Hanil Science Industrial, Korea) for 10 minutes with full speed. The levels of hematocrit were determined by calculation of the percent packed cells using standard methods (FIG. 8). Surprisingly, 2PEG-EPO had similar activity as 1 PEG-EPO.

6.8 Example 8

Hematocrit Induction by Various Forms of PEG-EPO

EPEG variants produced as described in Example 6 were further tested in the mouse model of hematocrit induction outlined in Example 7. The EPEG formulations selected for this assay each comprised approximately equal amounts of 1PEG-EPO and 2PEG-EPO: L33, Y5012, and X6012 (see Example 5). Their in vivo activity in terms of increased hematocrit was compared to that of PBS and native EPO. As described supra, each animal received approximately 5 μg of active agent, i.e., total protein As shown in FIG. 9, L33 and Y5012 have similar effect, with Y5012 slightly more active. Higher molecular weights of PEG did not further increase this activity. All EPEG formulations tested, except PEG-EPO modified with 40 k branched-PEG (X6012), demonstrated higher activity than the native EPO. The observed increase in activity relative to native EPO was independent of the use of SC-PEG or NHS-PEG, independent of the use of 12 kD or 20 kD PEG, and independent of the use linear or branched PEG.

6.9 Example 9

PEG-EPO is more Potent than Native EPO

L33 EPEG (i.e., linear SC-PEG-12K as activated PEG) was prepared according to Example 6 and protein concentration quantitated as described in section 6.3. The EPEG formulation was evaluated for in vivo activity according to the rat model according to Examples 7 and 8. Hematocrit levels were evaluated at 0, 2, 5, 7, 10 and 14 days. The native EPO for control was a recombinant human EPO (rhu-EPO) produced in a baculoviral expression system (as commonly known in the art, Rhu-EPO has the same amino acid sequences as the original human EPO, but the glycosylation pattern is different). EPEG or rhu EPO was administered to the rats as a single injection at a dosage of 2.5 or 5 µg per animal (each approximately 250 grams).

The hematocrit over a 14 day period is shown in FIG. 10. Administration of EPEG at 2.5 µg protein per rat exhibited the same effect as a 5 µg dosage of the control, rhu-EPO, suggesting that the EPEG of the invention is twice as potent as the control. With a 5 µg dosage, EPEG induced a hematocrit level of about 80%, almost twice that inducible by the un-modified, i.e., non-pegylated, EPO. Note that the control, rhu-EPO at 5 µg dose a exerted similar level hematocrit induction as the 2.5 µg dose. The result suggests that the control EPO had already reached a plateau in hematocrit induction at the tested dosages. These results were not surprising in that previous publications have claimed that EPO formulations fail to exhibit dose-response effects at greater than the 2.5 µg dosage tested. In contrast, the EPEG formulation of the invention exhibited a dose response effect at the higher dosage, resulting in substantially higher hematocrit induction that that achievable using the control compound. Accordingly, the EPEG formulations of the invention extend the both pharmaceutical properties and potential of the drug as currently understood in the art.

6.10 Example 10

Double Injections Demonstrating Long Lasting Effect of EPEG

The effect of serial administration of the EPEG formulations prepared according to Example 1, using reaction buffer containing DMSO, were assayed for in vivo activity according to the rat model of Examples 7 and 8.

Male Sprague-Dawley rats were divided into groups receiving either one (day 0) or a series of doses (day 0, 14) of EPEG formulations ("uninjected" or "injected," respectively in FIG. 11). Hematocrit levels were monitored over 21 days (FIG. 11). Relative to the surprising levels of hematocrit obtainable with a single 5 µg injection (FIG. 9 and FIG. 10), the activity of the EPEG formulations, i.e., hematocrit induction, becomes more pronounced using a serial injection dosing scheme (FIG. 10; EPEG 5 injected). Using the serial administration dosing scheme (each dose 5 µg), the hematocrit level approached the unexpected level of 90%, demonstrating improved activity relative to control compounds.

This disclosure describes only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention.

---

What is claimed is:

1. A plurality of erythropoietin (EPO) molecules, each conjugated to at least one polyethylene glycol (PEG) molecule, wherein more than 50% of said conjugation is at the α-amino group of the N-terminus, via a carbamate linkage, in preference to conjugation at lysinyl residues.

2. The plurality of conjugated molecules of claim 1, wherein said EPO protein is conjugated to one or two PEG molecules.

3. The plurality of conjugated molecules of claim 1, wherein said polyethylene glycol (PEG) is SC-PEG.

4. The composition of claim 1, wherein said EPO molecules are preferentially conjugated with PEG molecules at the N-terminus, in preference to occurring at the lysine-52, lysine-116 or lysine-154 residue.

5. The composition of claim 1, wherein at least 79% of said conjugation is at the α-amino group of the N-terminus of said protein.

6. The composition of claim 1, wherein 79% to 92% of said conjugation is at the α-amino group of the N-terminus of said protein.

7. The composition of claim 1, wherein no more than 10% of said conjugation is at lysine-116 of said protein.

8. The composition of claim 1, wherein no more than 3.5% of said conjugation is at lysine-154 of said protein.

9. The composition of claim 1, prepared by a process comprising:
(a) reacting EPO protein with activated water-soluble PEG in a reaction buffer comprising about 10 to about 40 percent (v/v) DMSO, and (b) removing substantially all unconjugated, water-soluble PEG.

10. The composition of claim 9, wherein the reaction buffer is an amine-free standard buffer comprising DMSO.

11. The composition of claim 9, wherein said activated water-soluble PEG is SC-PEG, SS-PEG, mPEG-imidate, or mPEG-cyanuric chloride.

12. The composition of claim 9, wherein said reaction buffer has a pH of about 6.5 to about 8.5.

13. A pharmaceutical composition comprising: (a) a plurality of EPO molecules, each conjugated to at least one polyethylene glycol (PEG) molecule, wherein more than 50% of said conjugation is at the α-amino group of the N-terminus, via a carbamate linkage, in preference conjugation at lysinyl residues of said protein; and (b) a pharmaceutically acceptable carrier.

14. The composition of claim 13, wherein said EPO protein is conjugated to one or two PEG molecules.

15. The composition of claim 13, wherein the polyethylene glycol is SC-PEG.

16. The composition of claim 13, wherein the polyethylene glycol molecule has a molecular weight in the range from about 10 kD to about 40 kD and is either linear or branched.

17. The composition of claim 13, wherein said pharmaceutically acceptable carrier is free of protein.

18. The composition of claim 13, wherein said EPO molecules are preferentially conjugated with PEG molecules at the N-terminus, in preference to occurring at the lysine-52, lysine-116 or lysine-154 residue.

\* \* \* \* \*